United States Patent
Gao et al.

(10) Patent No.: US 12,226,900 B2
(45) Date of Patent: Feb. 18, 2025

(54) SURGICAL ROBOT, AND CONTROL METHOD AND CONTROL DEVICE FOR ROBOT ARM THEREOF

(71) Applicant: Shenzhen Edge Medical CO., Ltd., Shenzhen (CN)

(72) Inventors: Yuanqian Gao, Shenzhen (CN); Guoqiang Ye, Shenzhen (CN)

(73) Assignee: Shenzhen Edge Medical CO., Ltd., Guangdong (CN)

( * ) Notice: Subject to any disclaimer, the term of this patent is extended or adjusted under 35 U.S.C. 154(b) by 493 days.

(21) Appl. No.: 17/640,908

(22) PCT Filed: Sep. 8, 2020

(86) PCT No.: PCT/CN2020/114114
§ 371 (c)(1),
(2) Date: Mar. 7, 2022

(87) PCT Pub. No.: WO2021/047521
PCT Pub. Date: Mar. 18, 2021

(65) Prior Publication Data
US 2022/0258333 A1  Aug. 18, 2022

(30) Foreign Application Priority Data
Sep. 10, 2019 (CN) .......................... 201910854105.6

(51) Int. Cl.
*A61B 34/37* (2016.01)
*B25J 3/00* (2006.01)
*B25J 9/10* (2006.01)

(52) U.S. Cl.
CPC ............... *B25J 9/106* (2013.01); *A61B 34/37* (2016.02); *B25J 3/00* (2013.01)

(58) Field of Classification Search
CPC ........ A61B 2034/301; A61B 2090/064; A61B 34/74; A61B 34/37; A61B 90/50; B25J 3/00; B25J 9/106
See application file for complete search history.

(56) References Cited

U.S. PATENT DOCUMENTS 10,820,949 B2 * 11/2020 Prisco .................... A61B 34/30
11,564,760 B2 * 1/2023 Steger .................... A61B 90/50
(Continued)

*Primary Examiner* — Jaime Figueroa
*Assistant Examiner* — Zachary Joseph Wallace
(74) *Attorney, Agent, or Firm* — ScienBiziP, P.C.

(57) ABSTRACT

A surgical robot and a control method and device for a robot arm (21) thereof. The surgical robot includes the robot arm (21) and the control device, the control device is configured for acquiring an external force applied on a power mechanism (22); acquiring an input operating command for task degrees of freedom of the power mechanism (22); combining the task degrees of freedom to analyze the external force to obtain target position and/or pose information of the power mechanism (22) at a base coordinate system, according to the target position and/or pose information, controlling a movement of joints of the robot arm to allow the power mechanism (22) to move within corresponding degrees of freedom. The operating command includes a completely matched first operating command, and a partially matched second operating command. The power mechanism (22) of the surgical robot can be precisely freely dragged or constraint control dragged.

20 Claims, 18 Drawing Sheets

(56) References Cited

U.S. PATENT DOCUMENTS

| | | | |
|---|---|---|---|
| 12,114,939 B2* | 10/2024 | Kostrzewski | A61B 34/20 |
| 2020/0289216 A1* | 9/2020 | Denlinger | A61B 34/37 |
| 2020/0289219 A1* | 9/2020 | Denlinger | B25J 13/02 |
| 2020/0289222 A1* | 9/2020 | Denlinger | B25J 9/1664 |
| 2020/0289223 A1* | 9/2020 | Denlinger | A61B 34/77 |
| 2020/0289227 A1* | 9/2020 | Jiang | A61B 34/76 |
| 2020/0297443 A1* | 9/2020 | Rosa | A61B 34/30 |
| 2020/0368982 A1* | 11/2020 | Valmassoi | B29C 66/8416 |
| 2020/0405375 A1* | 12/2020 | Shelton, IV | A61B 18/1815 |
| 2020/0405403 A1* | 12/2020 | Shelton, IV | A61B 17/3421 |
| 2020/0405405 A1* | 12/2020 | Shelton, IV | A61B 34/20 |
| 2020/0405414 A1* | 12/2020 | Shelton, IV | A61B 17/320092 |
| 2021/0022815 A1* | 1/2021 | Abbott | A61B 34/70 |
| 2021/0077213 A1* | 3/2021 | Gomez | A61B 34/35 |
| 2021/0186638 A1* | 6/2021 | Xia | A61B 34/76 |
| 2021/0259781 A1* | 8/2021 | Forstein | A61B 5/742 |
| 2022/0022985 A1* | 1/2022 | Liu | A61B 34/30 |
| 2022/0047345 A1* | 2/2022 | Choi | B25J 19/06 |
| 2022/0054209 A1* | 2/2022 | Lim | G16H 40/63 |
| 2022/0160458 A1* | 5/2022 | Tadano | A61B 90/50 |
| 2022/0192707 A1* | 6/2022 | Barakat | A61B 34/30 |
| 2022/0192777 A1* | 6/2022 | Kuroda | A61B 34/10 |
| 2022/0233820 A1* | 7/2022 | Clark | A61M 25/0113 |
| 2022/0400938 A1* | 12/2022 | Arai | G02B 23/24 |
| 2024/0050173 A1* | 2/2024 | Wilson | A61B 90/30 |

* cited by examiner

SURGICAL ROBOT, AND CONTROL METHOD AND CONTROL DEVICE FOR ROBOT ARM THEREOF

The present disclosure claims a priority of a Chinese patent application No. 201910854105.6, filed on Sep. 10, 2019 in China, titled "surgical robot, and control method and control device for robot arm thereof". All disclosures of the Chinese patent application may be quoted by the present disclosure.

FIELD

The subject matter herein generally relates to surgical systems, in particular to a surgical robot, a control method and a control device for a robot arm of the surgical robot.

BACKGROUND

Minimally invasive surgery refers to a surgical method of performing a procedure in a human body cavity using modern medical instruments such as laparoscopes, thoracoscopes, and so on. Compared with traditional surgery modes, minimally invasive surgery has advantages of being in little trauma, little pain, fast recovery, and the like.

With advances in science and technology, minimally invasive surgical technologies are increasingly mature and widely used. Minimally invasive surgical robots usually include a master console and a slave operating device, the master console includes a handle, a doctor sends a control command to the slave operating device by operating the handle, the slave operating device includes a robot arm and a plurality of operating arms arranged on a remote end of the robot arm. The operating arm has an end instrument. Before the surgical operation, the doctor needs to drag the robot arm until the remote end of the robot arm moves to a desired position and/or pose for aligning with the patient's surgical position.

However, when dragging the robot arm to the desired position, the load applied on the remote end of the robot arm is uncertain, that is, the external force an operator applied is not predetermined, resulting that a dragging sense is different from the operator's intention, and poor follow behavior of the robot arm may occur.

SUMMARY

Based on this, it is necessary to provide a surgical robot having a power mechanism can be better dragged, a control method thereof, and a computer readable storage medium.

In one aspect, a control method for a robot arm of a surgical robot is provided, the control method includes: according to installation state information and position state information inside of a power mechanism to obtain load parameters of the power mechanism at a corresponding state, the load parameters including quality parameters and centroid parameters; according to the load parameters to determine a load mechanics model at a six-dimensional force sensor coordinate system and corresponding to a load generated by the power mechanism; acquiring position information of joints of the robot arm and calculating a six-dimensional force/torque vector of the load based on the load mechanics model; acquiring a zero-biased six-dimensional force/torque vector and a total six-dimensional force/torque vector; according to the total six-dimensional force/torque vector, the zero-biased six-dimensional force/torque vector, and the six-dimensional force/torque vector of the load to calculate a six-dimensional force/torque vector of an external force applied on the power mechanism; analyzing the six-dimensional force/torque vector of the external force to obtain target position and/or pose information of the power mechanism at a base coordinate system of the robot arm, and according to the target position and/or pose information to control a movement of each of the joints of the robot arm to allow the power mechanism to reach a corresponding target position and/or pose.

In one embodiment, the installation state information is associated with an installation state of an operating arm at each power unit, the position state information is associated with a position state of each power unit relative to a rail; the installation state information includes information as to whether each power unit has installed the operating arm, and/or type information of the operating arm installed on each power unit.

In one embodiment, before the step of according to installation state information and position state information inside of a power mechanism to obtain load parameters of the power mechanism at a corresponding state, the control method includes: based on each installation state inside of the power mechanism, respectively determining the load parameters of the power mechanism at a corresponding installation state and a different internal position state; according to the determined load parameters of the power mechanism at the corresponding installation state and the different internal position state, respectively establishing a parameter calculation model corresponding to each of the installation states of the power mechanism.

In one of the embodiments, in the step of according to installation state information and position state information inside of a power mechanism to obtain load parameters of the power mechanism at a corresponding states, the control method including: acquiring the installation state information and the position state information inside of the power mechanism; according to the installation state information of the power mechanism to select a parameter calculation model; based on the selected parameter calculation model and the position state information of the power mechanism to calculate the load parameters of the power mechanism at the corresponding states.

In one of the embodiments, before the step of analyzing the six-dimensional force/torque vector of the external force to obtain the target position and/or pose information of the power mechanism at a base coordinate system of the robot arm, the control method includes: acquiring an input operating command associated with task degrees of freedom of the power mechanism; in the step of analyzing the six-dimensional force/torque vector of the external force to obtain the target position and/or pose information of the power mechanism at a base coordinate system of the robot arm, specially: combining the task degrees of freedom to analyze the six-dimensional force/torque vector of the external force to obtain the target position and/or pose information of the power mechanism at the base coordinate system of the robot arm to allow the power mechanism to move in corresponding task degrees of freedom.

In one of the embodiments, the operating command includes a first operating command and a second operating command. The first operating command is associated with a case of the task degrees of freedom that is completely matched with effective degrees of freedom of the robot arm, and the acquired target position and/or pose information analyzed according to the first operating command allows a free drag control of the power mechanism. The second operating command is associated with a case of the task degrees of freedom that is not completely matched with the effective degrees of freedom of the robot arm, but included in the effective degrees of freedom of the robot arm, and the acquired target position and/or pose information analyzed according to the second operating command allows a drag control of the power mechanism within a predetermined task degree of freedom.

In one of the embodiments, the second operating command is associated with a case of the task degrees of freedom of the power mechanism being selected from the effective degrees of freedom which is within the effective degrees of freedom of the robot arm and associated with pose degrees of freedom.

In one of the embodiments, in the step of analyzing the six-dimensional force/torque vector of the external force to obtain the target position and/or pose information of the power mechanism at the base coordinate system of the robot arm, specially: using a stiffness matrix with an adjustable control parameter to convert the six-dimensional force/torque vector of the external force to the target position and/or pose information of the power mechanism at the base coordinate system of the robot arm.

In another aspect, a control method for a robot arm of a surgical robot, the control method includes: acquiring a group of load parameters of each of six-dimensional force sensors, the group of the load parameters includes load parameters of each of links at a distal end of the six-dimensional force sensor, load parameters of the power mechanism are acquired according to installation state information and position state information inside of the power mechanism, and the load parameters includes a quality parameter and a centroid parameter. According to the group of the load parameters of each of the six-dimensional force sensors to determine a load mechanics model corresponding to a load due to the links at the distal end of the six-dimensional force sensor at a six-dimensional force sensor coordinate system; acquiring position information of each joint of the robot arm, based on the load mechanics model of each of the six-dimensional force sensors to respectively calculate a six-dimensional force/torque vector of the load of each of the six-dimensional force sensors; acquiring a zero-biased six-dimensional force/torque vector and a total six-dimensional force/torque vector, combining the six-dimensional force/torque vector of the load of each of the six-dimensional force sensors to calculate a six-dimensional force/torque vector of an external force applied on each of the six-dimensional force sensors. According to the calculated six-dimensional force/torque vector of the external force applied on each of the six-dimensional force sensors and the six-dimensional force/torque vector of the external force applied on an adjacent six-dimensional force sensor at a distal end of each of the six-dimensional force sensors to determine a force applied link, and calculate the six-dimensional force/torque vector of the external force applied on the force applied link. Analyzing the six-dimensional force/torque vector of the external force applied on the force applied link to obtain the target position and/or pose information of the force applied link at a corresponding coordinate system, and according to the target position and/or pose information to control a movement of the robot arm.

In one of the embodiments, the installation state information is associated with an installation state of an operating arm at each power unit, the position state information is associated with a position state of each power unit relative to a rail; the installation state information includes information as to whether each power unit has installed the operating arm, and/or type information of the operating arm installed on each power unit.

In one of the embodiments, before the step of according to the installation state information and position state information inside of a power mechanism to obtain load parameters of the power mechanism at a corresponding state, including: based on each the installation state inside of the power mechanism, respectively determining the load parameters of the power mechanism at the corresponding installation state and different internal position state; according to the determined load parameters of the power mechanism at the corresponding installation state and different internal position state, respectively establish a parameter calculation model corresponding to each of the installation states of the power mechanism.

In one of the embodiments, in the step of according to installation state information and position state information inside of a power mechanism to obtain load parameters of the power mechanism at a corresponding state, includes: acquiring the installation state information and position state information inside of the power mechanism; according to the installation state information of the power mechanism to select a parameter calculation model; based on the selected parameter calculation model and the position state information of the power mechanism to calculate the load parameters of the power mechanism at corresponding states.

In one of the embodiments, before the step of analyzing the six-dimensional force/torque vector of the external force applied on the force applied link to obtain the target position and/or pose information of the force applied link at the corresponding coordinate system, the control method includes: acquiring an input operating command associated with task degrees of freedom of the power mechanism; in the step of analyzing the six-dimensional force/torque vector of the external force applied on the force applied link to obtain the control command for controlling movement of the robot arm, specially: combining the task degrees of freedom of the power mechanism to analyze the six-dimensional force/torque vector of the external force to obtain the target position and/or pose information of the force applied link at the corresponding coordinate system.

In one of the embodiments, an operating command includes a first operating command and a second operating command. The first operating command is associated with a case of the task degrees of freedom that is completely matched with effective degrees of freedom of the robot arm, and the acquired target position and/or pose information analyzed according to the first operating command allows a free drag control of the power mechanism. The second operating command is associated with a case of the task degrees of freedom that is not completely matched with the effective degrees of freedom of the robot arm, but included in the effective degrees of freedom of the robot arm, and the acquired target position and/or pose information analyzed according to the second operating command allows a drag control of the power mechanism only within a predetermined task degree of freedom.

In one of the embodiments, the second operating command is associated with a case of the task degrees of freedom of the power mechanism being selected from the effective degrees of freedom which is within the effective degrees of freedom of the robot arm and associated with pose degrees of freedom.

In one of the embodiments, in a situation of the number of the force applied links is one, if the force applied link is the power mechanism, in the step of analyzing the six-dimensional force/torque vector of the external force applied on the force applied link to obtain target position and/or pose information of the force applied link at a corresponding coordinate system, and according to the target position and/or pose information to control a movement of the robot arm, the control method includes: combining the task degrees of freedom of the power mechanism to analyze the six-dimensional force/torque vector of the external force applied on the force applied link to obtain the target position and/or pose information of the power mechanism at the base coordinate system of the robot arm; and according to the target position and/or pose information to control a movement of the links of the robot arm to allow the power mechanism to reach a corresponding target position and/or pose.

In one of the embodiments, in a situation of the number of the force applied links is one, if the force applied link is not the power mechanism and an acquired input is the first operating command, in the step of analyzing the six-dimensional force/torque vector of the external force applied on the force applied link to obtain the target position and/or pose information of the force applied link at the corresponding coordinate system, and according to the target position and/or pose information to control a movement of the robot arm, the control method includes: analyzing the six-dimensional force/torque vector of the external force applied on the force applied link to obtain the target position and/or pose information of the force applied link at the base coordinate system of the robot arm; and according to the target position and/or pose information to control the movement of the force applied link of the robot arm and links adjacent to force applied link to allow the force applied link to reach a target position and/or pose.

In one of the embodiments, in a situation of the number of the force applied links is one, if the force applied link is not the power mechanism and the acquired input is the second operating command, in the step of analyzing the six-dimensional force/torque vector of the external force applied on the force applied link to obtain the target position and/or pose information of the force applied link at the corresponding coordinate system, and according to the target position and/or pose information to control a movement of the robot arm, the control method includes: analyzing the six-dimensional force/torque vector of the external force applied on the force applied link to obtain target position and/or pose information of the force applied link at the base coordinate system of the robot arm, and acquiring a current position and/or pose information of the power mechanism at the base coordinate system of the robot arm; converting the current position and/or pose information of the power mechanism at the base coordinate system of the robot arm to obtain target position and/or pose information of the power mechanism at a coordinate system of the force applied link and at when the force applied link reaches a target position and/or pose corresponding to the target position and/or pose information of the force applied link at the base coordinate system of the robot arm; according to the target position and/or pose information of the force applied link to control a movement of the force applied link and adjacent links to allow the force applied link to reach the corresponding target position and/or pose, and according the target position and/or pose information of the power mechanism to control a movement of the power mechanism and the links between the power mechanism and the force applied links to allow the power mechanism to maintain a current position and/or pose thereof.

In one of the embodiments, in a situation of the number of the force applied links is two or more, if the acquired input is the first operating command, in the step of analyzing the six-dimensional force/torque vector of the external force applied on the force applied link to obtain the target position and/or pose information of the force applied link at the corresponding coordinate system, and according to the target position and/or pose information to control a movement of the robot arm, the control method includes: analyzing the six-dimensional force/torque vector of the external force applied on the force applied link closest to a proximal end of the robot arm to obtain target position information of the force applied link at the base coordinate system of the robot arm; analyzing the six-dimensional force/torque vector of the external force applied on the force applied link farer away from the proximal end of the robot arm between each two adjacent force applied links to obtain the target position and/or pose information of the force applied link at a coordinate system of an adjacent force applied link; according to the target position and/or pose information of the force applied link closest to the proximal end of the robot arm to control a movement of the force applied link closest to the proximal end of the robot arm and adjacent links to allow the force applied link closest to the proximal end of the robot arm to reach the corresponding target position and/or pose, and according to the target position and/or pose information of farer away the proximal end of the robot arm between each two adjacent links to control a movement of the links between the force applied link farer away the proximal end of the robot arm and adjacent force applied link, to allow the force applied link farer away from the proximal end of the robot arm to reach a corresponding target position and/or pose.

In one of the embodiments, in a situation of the number of the force applied links is two or more, if the acquired input is the second operating command and the force applied links do not include the power mechanism, in the step of analyzing the six-dimensional force/torque vector of the external force applied on the force applied link to obtain the target position and/or pose information of the force applied link at the corresponding coordinate system, and according to the target position and/or pose information to control a movement of the robot arm, the control method includes: analyzing the six-dimensional force/torque vector of the external force applied on the force applied link closest to a proximal end of the robot arm to obtain the target position and/or pose information of the force applied link at the base coordinate system of the robot arm; analyzing the six-dimensional force/torque vector of the external force applied on the force applied link farer away from the proximal end of robot arm between each two adjacent force applied links to obtain the target position and/or pose information of the force applied link at a coordinate system of adjacent force applied link; acquiring a current position and/or pose information of the power mechanism at the base coordinate system of the robot arm, converting the current position and/or pose information of the power mechanism at the base coordinate system of the robot arm to obtain the target position and/or pose information of the power mechanism at the coordinate system of the adjacent force applied link and at when each of the links reaches a target position and/or pose corresponding to the target position and/or pose information of the corresponding coordinate system; according to the target position and/or pose information of the force applied link closest to the proximal end of the robot arm to control a movement of the force applied link closest to the proximal end of the robot arm and each of the links adjacent to the force applied link, to allow the force applied link closest to the proximal end of the robot arm to reach a corresponding target position and/or pose; according to the target position and/or pose information of the force applied link farer away the proximal end of the robot arm to control a movement of the force applied link farer away the proximal end of the robot arm and each of the links adjacent to the force applied link to allow the force applied link farer away the proximal end of the robot arm to reach a target position and/or pose; and according to the target position and/or pose information of the power mechanism to control a movement of the power mechanism and each of the links between the power mechanism and adjacent force applied link to allow the power mechanism to maintain current position and pose.

In one of the embodiments, in a situation of the number of the force applied links is more than two, if the acquired input is the second operating command and the force applied links include the power mechanism, in the step of analyzing the six-dimensional force/torque vector of the external force applied on the force applied link to obtain the target position and/or pose information of the force applied link at the corresponding coordinate system, and according to the target position and/or pose information to control a movement of the robot arm, the control method includes: analyzing the six-dimensional force/torque vector of the external force applied on the force applied link closest to the proximal end of the robot arm to obtain the target position and/or pose information of the force applied link at the base coordinate system of the robot arm; analyzing the six-dimensional force/torque vector of the external force applied on the power mechanism to obtain the target position and/or pose information of the power mechanism at the base coordinate system of the robot arm; analyzing the six-dimensional force/torque vector of the external force applied on the force applied link which is farer away the proximal end of the robot arm in each two adjacent links except the power mechanism to obtain the target position and/or pose information of the force applied link at a coordinate system of adjacent force applied link; converting the target position and/or pose information of the power mechanism at the base coordinate system of the robot arm to obtain the target position and/or pose information of the power mechanism at the coordinate system of adjacent force applied link and at when the force applied link adjacent to the power mechanism reach a target position and/or pose corresponding to the target position and/or pose information of the corresponding coordinate system; determining if the target position and/or pose information of the power mechanism at the coordinate system of adjacent force applied link is effective. If effective, according to the target position and/or pose information of the force applied link closest to the proximal end of the robot arm to control a movement of the force applied link closest to the proximal end of the robot arm and adjacent each link to allow the force applied link closest to the proximal end of the robot arm to reach the corresponding target position and/or pose; according to the target position and/or pose of the force applied link farer away the proximal end of the robot arm to control a movement of each of the links between the force applied link farer away the proximal end of the robot arm and adjacent force applied links to allow the force applied link farer away the proximal end of the robot arm to reach the corresponding target position and/or pose; according to the target position and/or pose information of the power mechanism to control a movement of the power mechanism and each of the links between the power mechanism and adjacent force applied link to allow the power mechanism to maintain its position while adjusting a pose thereof. If ineffective, combining the task degrees of freedom of the power mechanism to analyze the six-dimensional force/torque vector of the external force applied on the power mechanism to obtain the target position and/or pose information of the power mechanism at the base coordinate system of the robot arm, and according to the target position and/or pose information of the power mechanism to control a movement of each of the links of the robot arm to allow the power mechanism to maintain a position while adjusting a pose thereof.

In another aspect, a control device of an end instrument of a surgical robot is provided. The control device includes a storage medium configured for storing a computer procedure, a processor configured for loading and carrying out the computer procedure, and the computer procedure is loaded by the above processor and carries out the above steps.

In another aspect, a surgical robot is provided. The surgical robot includes a robot arm and a control device, the robot arm includes a plurality of links connected by joints. The link at a remote end of the robot arm is configured as a power mechanism, the power mechanism and adjacent links are connected by six-dimensional sensors. The power mechanism includes rails and power units slidable on the rails, and the power units are configured for installing and driving an operating arm for surgical operation. The control device is configured for carrying out the above control steps.

In another aspect, the present disclosure provides a surgical robot including: a robot arm having a plurality of links connected by joints, and the link at a remote end of the robot arm is configured as a power mechanism; and a control device coupled to the robot arm, the control device is configured for: acquiring an external force applied on the power mechanism; acquiring an input operating command associated with task degrees of freedom of the power mechanism; combining the task degrees of freedom of the power mechanism to analyze the target position and/or pose information of the power mechanism at a base coordinate system of the robot arm, and according to the target position and/or pose information to control a movement of each of the links of the robot arm, thus the power mechanism moves within corresponding task degrees of freedom to reach a corresponding target position and/or pose. The operating command includes a first operating command or a second operating command, the first operating command is associated with a case of the task degrees of freedom completely matched with effective degrees of freedom of the robot arm, and according to the target position and/or pose information acquired by analyzing the first operating command allows a free drag control of the power mechanism; the second operating command is associated with a case of the task degrees of freedom not completely matched with the effective degrees of freedom of the robot arm, but included in the effective degrees of freedom of the robot arm, and according to the target position and/or pose information acquired by analyzing the second operating command allows only a drag control of the power mechanism within a predetermined task degree of freedom.

In another aspect, the present disclosure provides a surgical robot including: a robot arm having a plurality of links connected by joints, and the link at a remote end of the robot arm is configured as a power mechanism; and a control device coupled to the robot arm, the control device is configured for: detecting a force applied link among the links and acquiring an external force applied on the force applied link; acquiring an input operating command associated with task degrees of freedom of the power mechanism; combining the task degrees of freedom of the power mechanism to analyze the external force applied on the force applied link to acquire the target position and/or pose information of the force applied link at a corresponding coordinate system, and according to the target position and/or pose information to control a corresponding movement of the robot arm. The operating command includes a first operating command or a second operating command, the first operating command is associated with a case of the task degrees of freedom completely matched with effective degrees of freedom of the robot arm, and according to the target position and/or pose information acquired by analyzing the first operating command allows a freely drag control of the power mechanism; the second operating command is associated with a case of the task degrees of freedom not completely matched with the effective degrees of freedom of the robot arm, but included in the effective degrees of freedom of the robot arm, and according to the target position and/or pose information acquired by analyzing the second operating command can only allow a drag control of the power mechanism within a predetermined task degree of freedom.

In another aspect, the present disclosure provides a control method for a robot arm of a surgical robot, the robot arm includes a plurality of links connected by joints, and the link at a remote end of the robot arm is configured as a power mechanism, the control method includes: determining a force applied link among the links and acquiring an external force applied on the force applied link; acquiring an input operating command associated with task degrees of freedom of the power mechanism; combining the task degrees of freedom of the power mechanism to analyze the external force applied on the force applied link to acquire the target position and/or pose information of the force applied link at a corresponding coordinate system, and according to the target position and/or pose information to control a corresponding movement of the robot arm. The operating command includes a first operating command or a second operating command, the first operating command is associated with a case of the task degrees of freedom completely matched with effective degrees of freedom of the robot arm, and according to the target position and/or pose information acquired by analyzing the first operating command can freely drag control the power mechanism; the second operating command is associated with a case of the task degrees of freedom not completely matched with the effective degrees of freedom of the robot arm, but included in the effective degrees of freedom of the robot arm, and according to the target position and/or pose information acquired by analyzing the second operating command can only drag control the power mechanism within a predetermined task degree of freedom.

The present disclosure has the following beneficial effects:

By determining accurately load parameters of a load caused by a remote structure of a force component, to facilitate accurately determine a six-dimensional force/torque vector of the load, thus accurately determining the six-dimensional force/torque vector of an external force of the force component, which in turn will help drag the force component according to the external force. The tactile feeling for dragging is good, and the follow behavior is excellent.

DETAILED DESCRIPTION

For ease of understanding of the present application, the present application will be described more fully hereinafter with reference to the associated drawings. Preferred embodiments of the present application are set forth in the accompanying drawings. This application may, however, be embodied in many different forms and is not limited to the embodiments described herein. Rather, these embodiments are provided for the purpose of providing a more thorough and thorough understanding of the disclosure of the present application.

It should be noted that when an element is referred to as being "disposed on" another element, it may be directly on the other element or intervening elements may also be present. When an element is considered to be "connected" to another element, it may be directly connected to another element or intervening elements may be present at the same time. When an element is considered to be "coupled" to another element, it may be directly coupled to another element or intervening elements may be present at the same time. As used herein, the terms "vertical", "horizontal", "left", "right" and the like are intended for purpose of illustration only and are not intended to be limiting. As used herein, the terms "distal end" and "proximal end" are common terms in the art of interventional medical devices, where "distal end" refers to the end far away from the operator during the surgical procedure, and the "proximal end" refers to the end close to the operator during the surgical procedure.

Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes all combinations of one or more of the associated listed items.

Figure 1:
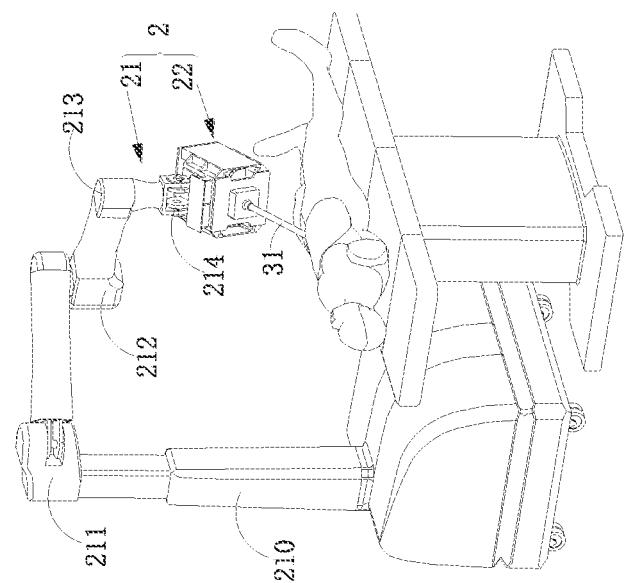
FIG. 1 is a schematic structural view of a surgical robot according to an embodiment of the present disclosure.
Figure 1:
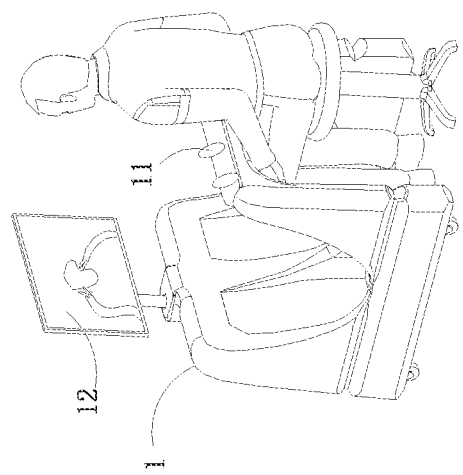
Figure 2:
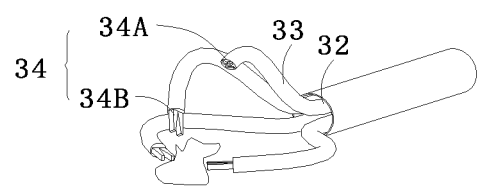
FIG. 2 is a schematic partial view of the surgical robot of FIG. 1.
Figure 3:
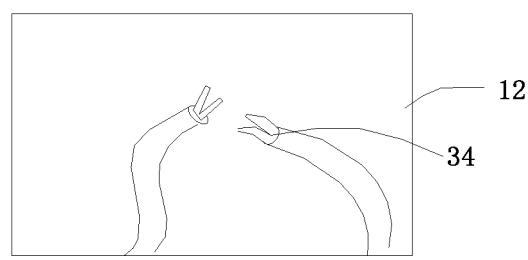
FIG. 3 is a schematic partial view of the surgical robot of FIG. 1.

Referring to FIGS. 1 to 3, a schematic structural view of a surgical robot according to an embodiment and a partial schematic view thereof are illustrated.

A surgical robot includes a master console 1 and a slave operating device 2. The master console 1 has a controller 11 and a display 12. A doctor gives a control command to the slave operating device 2 by operating the controller 11, to make the slave operating device 2 perform the corresponding operation according to the control command of the doctor given to the controller 11, and the surgical area is observed by the display 12. In particular, the controller 11 can freely move and rotate, thus the doctor has a greater operating space, for example, the controller 11 can be connected to the master console 1 by a connection wire, or by a rotatable link connected to the master console 1. The slave operating device 2 includes a robot arm 21 having a plurality of links connected by joints, and the link at a remote end of the robot arm 21 is a power mechanism 22, and the power mechanism 22 is configured for installing and driving operating arms 31 each having an end instrument 34.

In one embodiment, the joints of the robot arm 21 can be remotely operated by the controller 11 to make the power mechanism 22 move to a desired position and/or pose.

In another embodiment, the power mechanism 22 can be dragged to allow the joints of the robot arm 21 to linkably move, such that the power mechanism 22 moves to a desired position and/or pose. The present disclosure discloses how the power mechanism 22 can be dragged to a desired position and/or pose.

Figure 4:
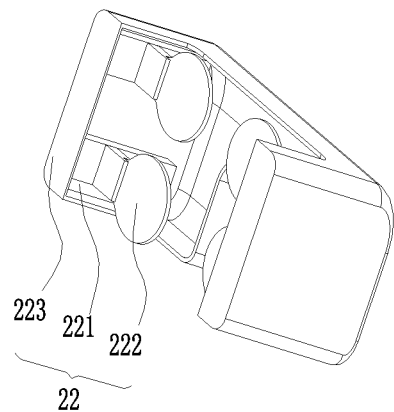
FIG. 4-FIG. 7 are schematic views showing different installation states and position states of a power mechanism.

As shown in FIG. 4, the power mechanism 22 includes an outer casing 223 connected to a remote end of the robot arm 21, the outer casing 223 has rails 221, each of the rails 221 is for a power unit 222 slidably mounted thereon, and the power units 222 are configured for mounting and driving the operating arms 31 each having the end instrument 34. The number of rails 221 is one or more (four shown in FIG. 4), and the number of power units 222 is the same as the number of rails 221. The rail 221 is typically a linear guide, and the power unit 222 performs a linear movement on the rail 221, in particular, there may be a power portion (not shown) located on the rail 221 for driving the power unit 222 slide on the rail 221. For ease of dragging, a handle (not shown) can be installed in the outer casing 223.

An internal installation state and position state of the power mechanism 22 may easily change a load of the power mechanism 22 to affect the drag of the power mechanism 22. The installation state inside the power mechanism 22 is specifically associated with whether or not the operating arm 31 is installed and/or associated with a type of operation arm 31, and the internal position state of the power mechanism 22 is specifically associated with a position of the respective power unit 222 relative to the corresponding rail 221.

Figure 5:
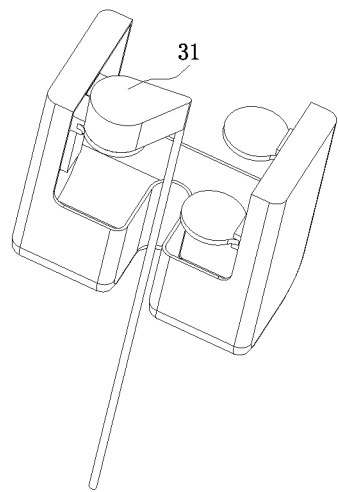
Figure 6:
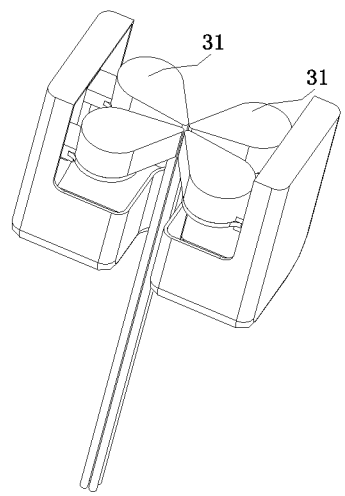
Figure 7:
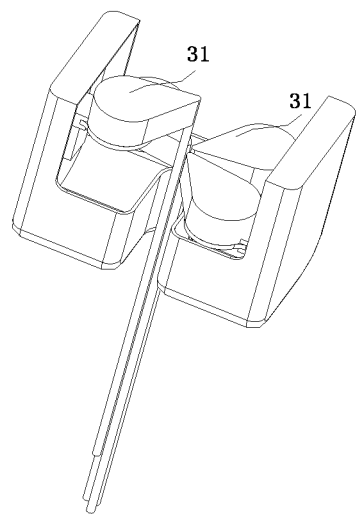

Exemplary, there is no operating arm 31 installed on each of the power units 222; in FIG. 5, an operating arm 31 is installed on the power unit 222; in FIG. 6, each of the four power units 222 has an operating arm 31 installed thereon, and the four power units 222 are at a same position state relative to the respective rails 221; in FIG. 7, the four power units 222 each are installed with an operating arm 31, but a position state of one of the power units 222 relative to the respective rail 221 is different from other position state of the remaining power units 222 relative to the respective rails 221. In FIG. 4 to FIG. 7, it is assumed that the type of operation arms 31 installed on the power units 222 does not affect the load change, thus substantially reflecting different state changes inside the power mechanism 22, which can cause changes of the load of a six-dimensional sensor. In fact, the difference in the type of operation arms 31 installed on the power units 222 also affects the load change, and it can be considered when using the control method below.

Figure 8:
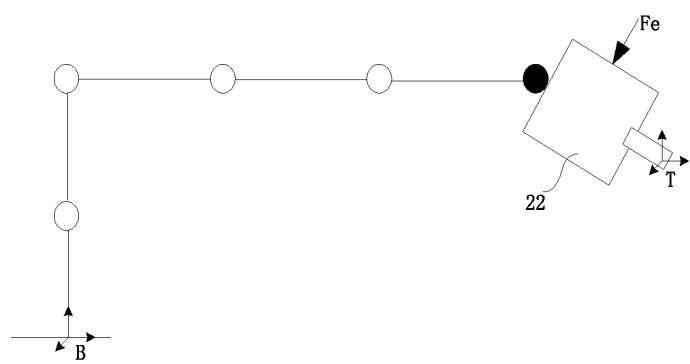
FIG. 8 is a schematic operating view under a configuration of a robot arm shown in FIG. 1.

In one embodiment, as shown in FIG. 8, the power mechanism 22 is connected to an adjacent link by a six-dimensional sensor, and the six-dimensional sensor is connected to a control device of the surgical robot, in particular, the hollow circle "○" refers to the joint that does not have a six-dimensional sensor installed thereon, and the solid circle "●" refers to the joint that have a six-dimensional sensor installed thereon. More specifically, the six-dimensional sensor is arranged on a joint of the remote end of the robot arm 21 and is rigidly attached to the outer casing 223 of the power unit 222. For such six-dimensional sensor, the entire power mechanism 22 constitutes its load, and the six-dimensional sensor can monitor all force/torque vectors in the load side.

Figure 9:
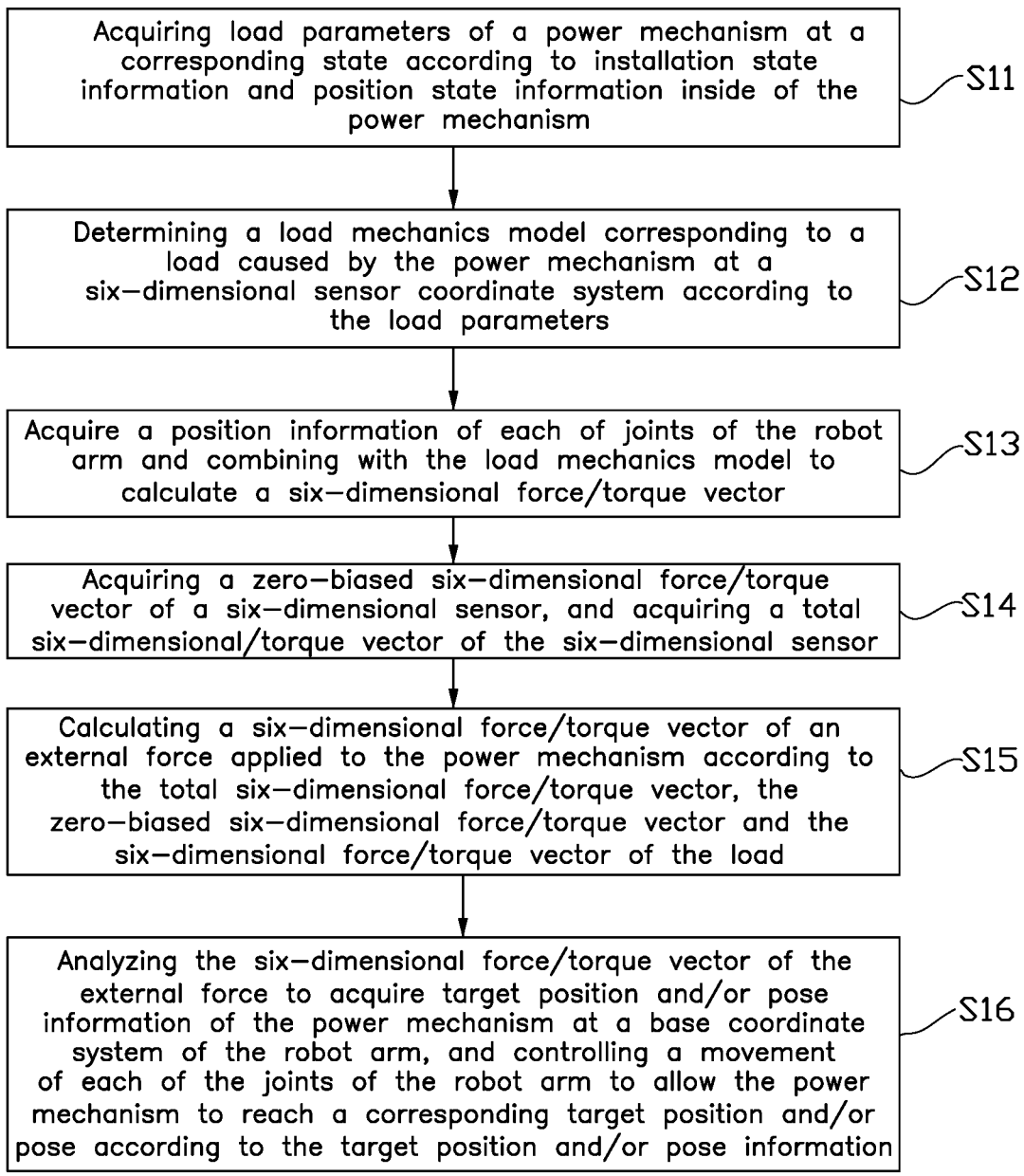
FIG. 9-FIG. 12 are flow charts of control methods according to different embodiments of the present disclosure.

As shown in FIG. 9, in a control method of a robot arm of a surgical robot in one embodiment, the control method includes:

Step S11, according to installation state information and position state information inside of a power mechanism, acquiring load parameters of the power mechanism at a corresponding state.

The load parameters include quality parameters and centroid parameters.

Step S12, according to the load parameters, determining a load mechanics model corresponding to a load caused by the power mechanism at a six-dimensional sensor coordinate system.

Step S13, acquiring position information of each of joints of the robot arm and combining with the load mechanics model to calculate a six-dimensional force/torque vector.

Step S14, acquiring a total six-dimensional/torque vector of a six-dimensional sensor, and acquiring a zero-biased six-dimensional force/torque vector of the six-dimensional sensor. Specifically, step S14 can only be placed before step S15.

Specifically, a corresponding six-dimensional force/torque vector can be obtained by decoupling and filtering data acquired by the six-dimensional sensor. The zero-biased six-dimensional force/torque vector can be obtained in advance.

Step S15, according to the total six-dimensional force/torque vector, the zero-biased six-dimensional force/torque vector, and the six-dimensional force/torque vector of the load, calculating a six-dimensional force/torque vector of an external force applied to the power mechanism.

Step S16, analyzing the six-dimensional force/torque vector of the external force to acquire target position and/or pose information of the power mechanism at a base coordinate system of the robot arm, and according to the target position and/or pose information, controlling a movement of each of the joints of the robot arm to allow the power mechanism to reach a corresponding target position and/or pose.

Figure 10:
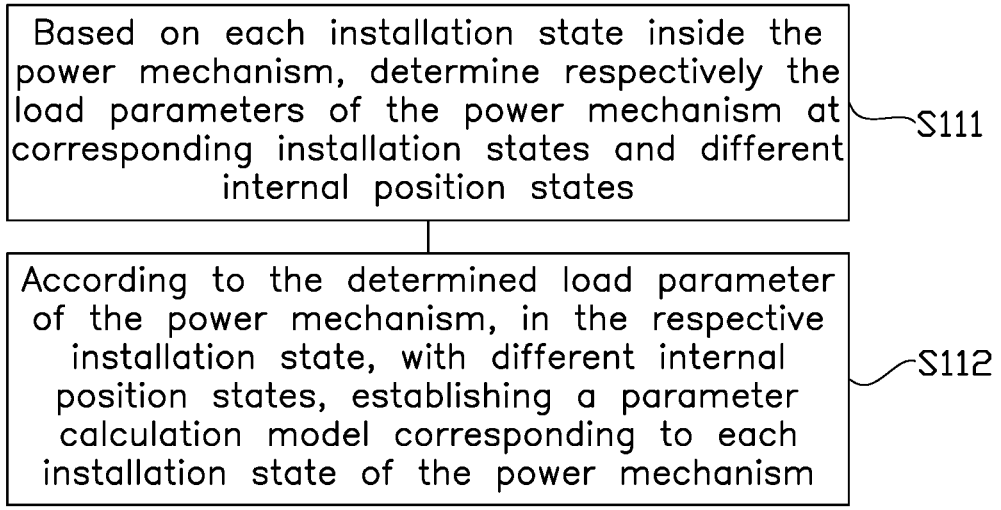

In one embodiment, as shown in FIG. 10, specifically before step S11, the control method includes:

Step S111, based on each of installation states inside the power mechanism, determining respectively the load parameters of the power mechanism at corresponding installation states and different internal position states.

In particular, in a same installation state, the more position states selected, the more accurate the determined load parameters. In particular, the operating arm 31 on each of the power units 222 is installed by operators, and a position change of the power unit 222 relative to the rail 221 can be carried out by controlling the power unit 222 slidable on the rail 221, for example, the control device can generate a few position parameters for driving the power unit 222 slide on the rail 221 to corresponding positions.

Step 112, according to the determined load parameter of the power mechanism, in the respective installation state, with the different internal position states, establishing a parameter calculation model corresponding to each of the installation states of the power mechanism.

Figure 11:
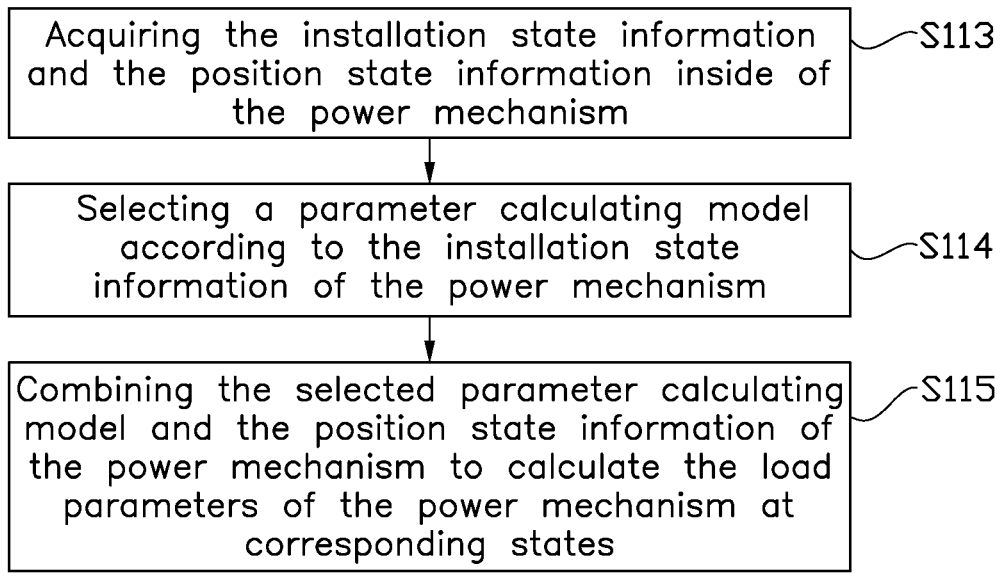

Furthermore, as shown in FIG. 11, in step S11, the control method includes:

Step 113, acquiring the installation state information and the position state information inside of the power mechanism.

Step 114, according to the installation state information of the power mechanism, selecting a parameter calculating model.

Step 115, combining the selected parameter calculating model and the position state information of the power mechanism to calculate the load parameters of the power mechanism at corresponding states.

In step S113, in order to acquire the installation state information of whether or not each of the power units 222 has installed the operating arm 31, a detecting mechanism can be provided on each of the power units 222, which is used to detect whether or not the power unit 222 has installed the operating arm 31, the detecting mechanism can be selected from a proximity sensor, a pressure sensor, a photoelectric sensor, and the like.

In step S113, in order to acquire type information of the operation arm 31 installed on each of the power units 222 in the installation state information, in one aspect, a memory having the type information of the corresponding operating arm 31 can be configured on each of the operating arms 31, and in the power mechanism 22, for example, the power unit 222 is provided with a data interface connected to the control device in the surgical robot, when the operating arm 31 is attached to the power unit 222, the data interface is connected to the memory, and then the type information of the operating arm 31 is read through the data interface. On the other hand, an electronic tag that has the type information of the corresponding operating arm 31 can be configured on each of the operating arms 31, and correspondingly in the power mechanism 22 is provided with a reader connected to the control device in the surgical robot, when the operating arm 31 is installed on the power unit 222, the reader inducts the electronic tag and read the type information of the operating arm 31 therefrom, the electronic tag may be an RFID electronic tag, an NFC electronic tag, etc., accordingly the reader can be RFID reader or NFC reader. In particular, the type of operation arm 31 is mainly related to the type of end instrument 34 thereon, or it may be related to the type of structure of the operating arm 31 itself. The end instrument 34 includes an image end instrument 34A and an operating end instrument 34B as shown in FIG. 2. Generally, the image end instruments 34a have fewer types, and the operation end instruments 34B can have various types.

In step S113, in order to acquire the position information of each power unit 222 with respect to the respective rail 221 in the position state information, a position sensor can be set in driving portions for driving the power unit 222 slide relative to the rail 221 to detect the position information. The driving portions typically include a motor and an encoder, and the encoder can be used as a position sensor to obtain the above-described position information.

Specifically, the number of parameter calculation models mentioned in step S112 is consistent with the number of the internal installation states of the power mechanism 22. It is assumed that the number of the power units 222 of the power mechanism 22 is N, and it is assumed that the number of operating arms 31 is m, which may have the following number of installation states depending on the setting condition.

Example 1, if only whether each of the power units 222 has installed the operating arm 31 is considered. At this situation, a total 2n installation states can be obtained, and accordingly there are 2n parameter calculation models.

Example 2, if each of the power units 222 has installed the operation arm 31, and the types of the operating arms 31 are considered. At this situation, a total $(m+1)^n$ installation states can be obtained, and accordingly there are $(m+1)^n$ parameter calculation models.

In particular, in the example 2:

If only different power units 222 are allowed to install different types of operating arms 31, when M≥N, a total of $1+C_m^1 A_n^1 + C_m^2 A_n^2 + L\ C_m^n A_n^n$ installation states can be obtained, and accordingly there are $1+C_m^1 A_n^1 + C_m^2 A_n^2 + L\ C_m^n A_n^n$ parameter calculation models; When m<n, a total of $1+C_m^1 A_n^1 + C_m^2 A_n^2 + L\ C_m^m A_n^m$ installation states can be obtained, and accordingly there are $1+C_m^1 A_n^1 + C_m^2 A_n^2 + L\ C_m^m A_n^m$ parameter calculation models.

If only one power unit 222 is allowed to install an operating arm 31 having an image end instrument 34A, a total of $n \times m^{n-1}$ installation states can be obtained, and accordingly there are $n \times m^{n-1}$ parameter calculation models; furthermore, under this condition, if one of the power units 222 at a specific position is allowed to install the operating arm 31 having the image end instrument 34A, and if it has been installed, a total of $m^{n-1}$ installation states can be obtained, and accordingly there are $m^{n-1}$ parameter calculation models.

By limiting different conditions, the number of identifiable installation states can be reduced, accordingly thereby reducing the number of parameter calculation models.

The establishment of the parameter calculation model referred to in step S112 includes the following steps:

Defining a mathematical formula of the parameter calculation model;

Sampling and calculating input and output data for the parameter calculation model; and According to the above sampled and calculated input and output data of the parameter calculation model, estimating model parameters, thereby determining the parameter calculation model.

In particular, this parameter calculation model may be in the form of MISO (Multi-input single output) or MIMO (multi-input multi-output) form, which can be determined according to the coupling states of the model parameters of selected load mechanics model. In addition, a learning model can be defined, corresponding to different installation states, by using machine learning and using as more the input and output data associated with the sampling parameter calculation model to obtain the parameter calculation model. This parameter calculation model can be linear or non-linear, which can be determined by preliminary mechanics analysis or test data. If it is linear, a minimum multiplier or greatly likelihood, etc. is used to determine the model parameters of the parameter calculation model; if it is non-linear, a nonlinear optimization calculation method such as Newton Gaussi can determine the model parameters of the parameter calculation model.

Step S112, the parameter calculation model and the corresponding installation state information thereof can be associated with the data structure such as a parameter dictionary, a list, and the like to facilitate selection in subsequent step S114.

The load parameters of the load mechanics model for determining a six-dimensional force/torque vector of the load described in the above step S12 can be calculated based on the parameter calculation model. This parameter calculation model exemplary can be represented as $P_{load} = f(S'P')$, wherein $P_{load}$ refers to the load parameters, S' refers to the position state information of each power unit relative to the respective rail, and P' refers to the model parameters of the parameter calculation model.

Exemplary, assuming $P_{load}=k_1 S'_1+k_2 S'_2+ \ldots +k_n S'_n+k_{n+1}$, n refers to the number of power units 222, and P' refers to the model parameters of the parameter calculation model, that is $k_1 \sim k_{n+1}$, $S'_1 \sim S'n$, respectively presents the position state information of each power unit 222 relative to the rail 221, wherein $K_{n+1}$ refers to a zero state parameter of the parameter calculation model, and $K_1 \sim K_{n+1}$ all are obtained by detecting (such as calibration and/or identification).

The above load mechanics model exemplarily represented by $Fm=f(S, P_{load})$, wherein $F_m$ refers to the six-dimensional force/torque vector of the load, and S represents the position state information of each joint in the robot arm.

The position state information of each of the joints in the robot arm 21 can be acquired by a position sensor disposed at each joint, and the position sensor can also be an encoder of a driving portion (i.e., a motor having an encoder) which is configured for driving the joints to move.

The above step S15 can be obtained according to the following formula:

$$F_e = F_s - F_m - F_0$$

$F_e$ refers to a six-dimensional force/torque vector of an external force, $F_s$ refers to a total six-dimensional force/torque vector, $F_m$ refers to a six-dimensional force/torque vector of a load, $F_0$ refers to a zero-biased six-dimensional force/torque vector. Wherein, the $F_e$ calculation needs $F_s$, $F_m$ and $F_0$ calculation performed under the same reference coordinate system, which is usually calculated directly under the sensor coordinate system of the six-dimensional sensor.

Figure 12:
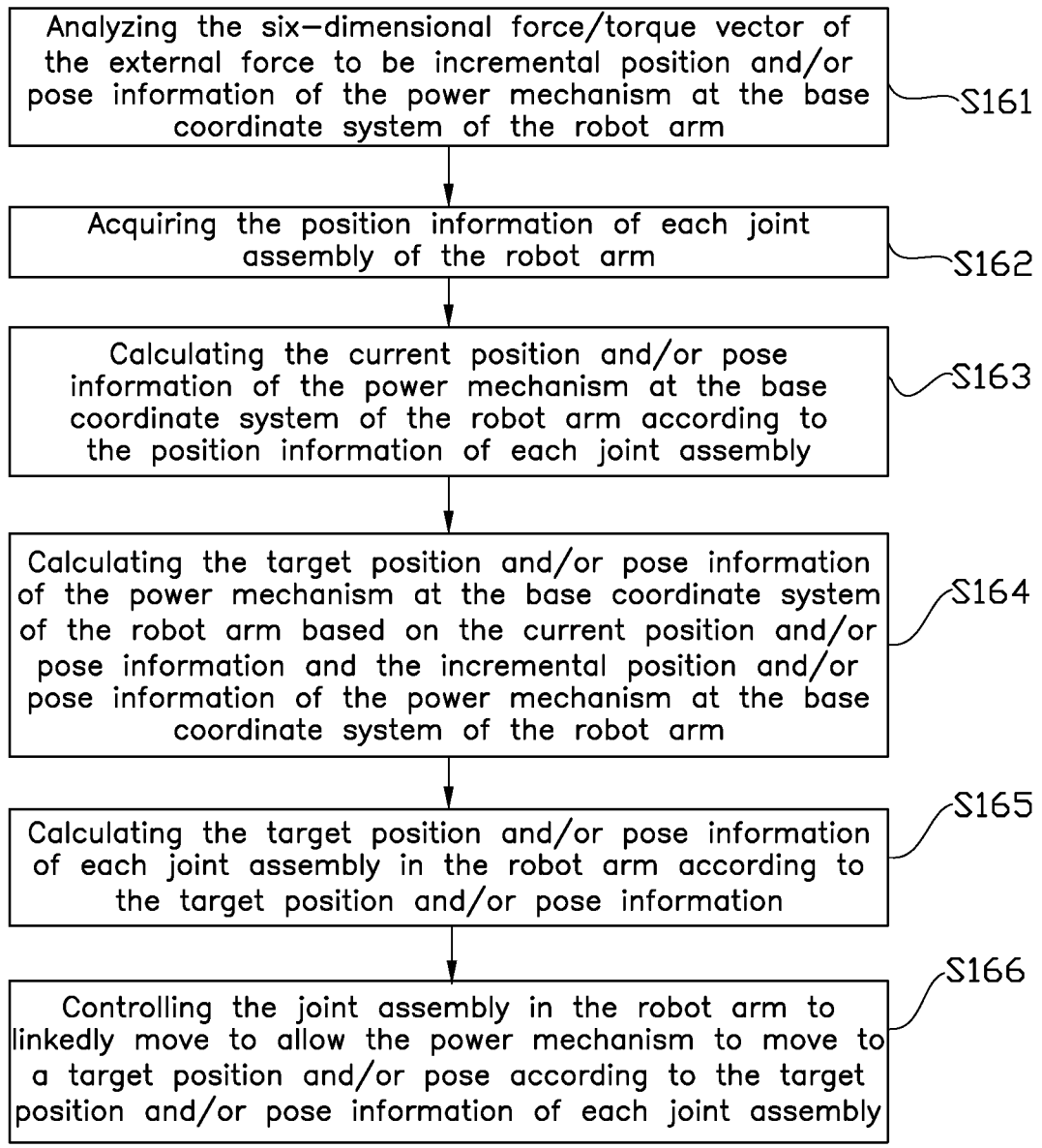

As shown in FIG. 12, in step S16, the control method includes:

Step S161, analyzing the six-dimensional force/torque vector of the external force to be incremental position and/or pose information of the power mechanism at the base coordinate system of the robot arm.

Step S162, acquiring the position information of each joint assembly of the robot arm.

Figure 13:
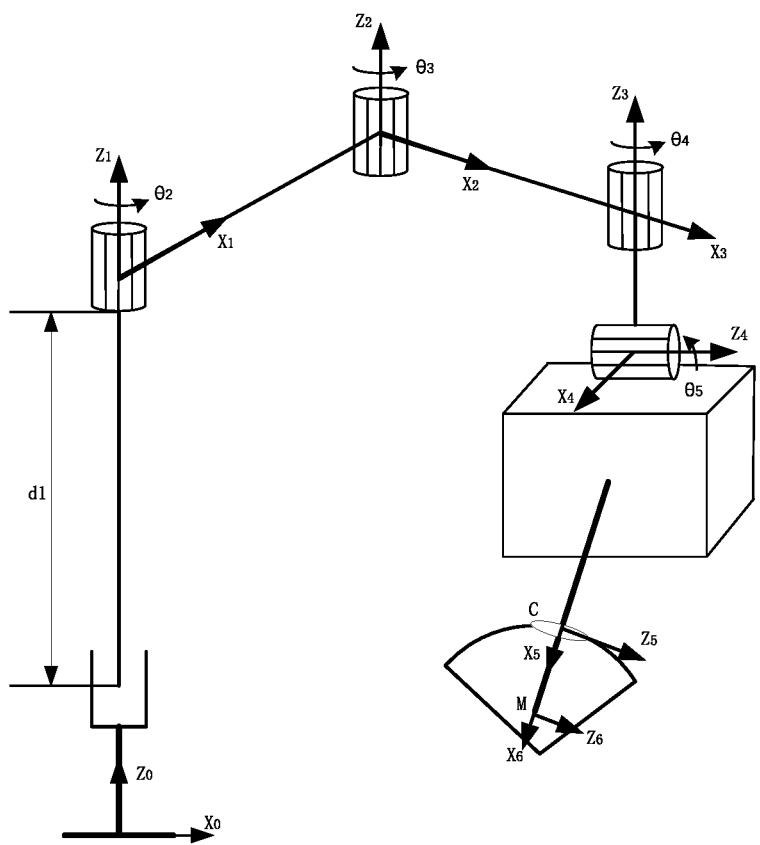
FIG. 13 is a principle structural view of the robot arm of FIG. 1.

In the embodiment illustrated in FIGS. 1 and 13, the robot arm 21 has 5 degrees of freedom, and can be collected such a group of position information $(d_1, \theta_2, \theta_3, \theta_4, \theta_5)$ by each of the position sensors.

Step S163, according to the position information of each joint assembly, calculating current position and/or pose information of the power mechanism at the base coordinate system of the robot arm.

In particular, the current position and/or pose information of the power mechanism at the base coordinate system of the robot arm actually refers to current position and/or pose information of a tool coordinate system of the robot arm at the base coordinate system, which usually can be calculated in conjunction with forward kinematics. Establish a kinematics model of the fixed point (i.e., the C point, the origin of the tool coordinate system of the robot arm 21 is at the fixed point) of the robot arm 21 to the base of the robot arm 21, output model conversion matrix $^0_C T$ of the C point to the base. The calculation method is $^0_C T = ^0_1 T\, ^1_2 T\, ^2_3 T\, ^3_4 T\, ^4_C T$.

Step S164, based on the current position and/or pose information and the incremental position and/or pose information of the power mechanism at the base coordinate system of the robot arm, calculating the target position and/or pose information of the power mechanism at the base coordinate system of the robot arm.

Figure 14:
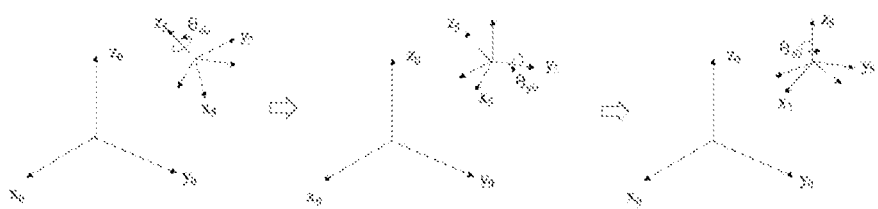
FIG. 14 is a schematic analyzing view of a space motion angle by a control method of present disclosure.

In particular, according to the model conversion matrix $^0_C T$ of the C point to the base, the position and/or pose information of the C point at the fixed coordinate system is acquired. It is assumed that the C point position is unchanged, rotate the coordinate system of the C point, to reach the position and/or pose described by the model conversion matrix to obtain a rotary axis angle $[\theta_{x0}, \theta_{y0}, \theta_{z0}]$, as shown in FIG. 14. Wherein $\theta_{x0}$ refers to a rolling angle, $\theta_{y0}$ refers to a yaw angle, $\theta_{z0}$ refers to a pitch angle, and in the robotic arm 21 shown in FIGS. 1 and 13, lacking the freedom of the rolling angle results in $\theta_{x0}$ unadjustable.

Step S165, according to the target position and/or pose information, calculating the target position and/or pose information of each joint assembly in the robot arm.

The above step is typically calculated in combination with inverse kinematics.

Step S166, according to the target position and/or pose information of each joint assembly, controlling the joint assembly in the robot arm to linkedly move to allow the power mechanism to move to a target position and/or pose.

This step can use CSP (period synchronization location) mode and combined with PID adjustment to control the joint assembly of the robot arm 21 linkedly move.

In this embodiment, in step S16 of analyzing the six-dimensional force/torque vector to obtain the target position and/or pose information of the power mechanism at the base coordinate system of the robot arm, an input operating command associated with task degrees of freedom of the power mechanism can be acquired, and combined with the task degrees of freedom to analyze the six-dimensional force/torque vector of the external force to obtain the target position and/or pose information of the power mechanism at the base coordinate system of the robot arm.

In particular, the operating command includes a first operating command and the second operating command. The first operating command is associated with a case that the task degrees of freedom are completely matched with effective degrees of freedom of the robot arm 21, and the acquired target position and/or pose information analyzed by the first operating command can freely drag the power mechanism 22. The second operating command is associated with a case that the task degrees of freedom are not completely matched with the effective degrees of freedom of the robot arm 21, but are included in the effective degrees of freedom of the robot arm 21, the acquired target position and/or pose information analyzed by the second operating command can drag the power mechanism 22 within a predetermined degree of freedom. Furthermore, the second operating command is associated with a case of the task degrees of freedom of the power mechanism 22 being selected from effective degrees of freedom which is within the effective degrees of freedom of the robot arm 21 and associated with pose degrees of freedom thereof.

Specifically, the task degrees of freedom of the power mechanism 22 can be understood to be allowable degrees of freedom of the power mechanism 22 in the Cartesian space, which is at most 6 degrees of freedom. The power mechanism 22 has effective degrees of freedom in the Cartesian space, and the effective degrees of freedom of the power mechanism 22 is associated with the configuration (i.e., structural features) of the robot arm 21, the effective degrees of freedom of the power mechanism 22 can be understood to be achievable effective degrees of freedom of the power mechanism 22 in Cartesian space, which is at most 6 degrees of freedom. The task degrees of freedom of the power mechanism 22 is allowable movement degrees of freedom.

The six-dimensional force/torque vector of the external force can be analyzed according to the task degrees of freedom (configuration information) in step S16, and then the analyzed six-dimensional force/torque vector of the external force can be mapped to the incremental position and/or pose information of the power mechanism. For example, the task degrees of freedom allows [x, y, z] degrees of freedom in [x, y, z, α, β, γ] position and/or pose information, thus in analyzing the six-dimensional force/torque of external force, only the six-dimensional force/torque vectors of the external force corresponding to the [x, y, z] three degrees of freedom are analyzed, and the six-dimensional force/torque vectors of the external force corresponding to the [x, y, z] three degrees of freedom are mapped to the incremental position and/or pose information of the power mechanism 22.

Of course, it is also possible to completely analyze the six-dimensional force/torque vector of the external force, and then according to the task degrees of freedom, map the analyzed six-dimensional force/torque vector of the external force to be the incremental position and/or pose information of the power mechanism 22. For example, the task degrees of freedom also allows the [x, y, z] degrees of freedom in the [x, y, z, α, β, γ] position and/or pose information, thus in analyzing the six-dimensional force/torque of the external force, the six-dimensional force/torque vectors of the external force corresponding to the [x, y, z, α, β, γ] six degrees of freedom are all analyzed, and then the six-dimensional force/torque vectors of the external force corresponding to the [x, y, z] degrees of freedom are mapped to the incremental position and/or pose information of the power mechanism 22.

For example, in the robot arm 21 shown in FIG. 13, the effective degrees of freedom information of the robot arm 21 includes [x, y, z, α, β], which is caused by the joint assemblies 210 to 214, and do not include degrees of freedom in rolling angle γ.

If the configuration information of the task degrees of freedom of the power mechanism 22 is [x, y, z, α, β], accordingly the configuration information of the task degrees of freedom of the power mechanism 22 is completely matched with the effective degrees of freedom information of the robot arm 21, in this situation, the power mechanism 22 is in free control, and it is possible to control the power mechanism 22 to be moved to accommodate the operating chamber arrangement, which corresponds to the case associated with the first operating command.

When the configuration information of the task degrees of freedom of the power mechanism 22 is [x, y, z, α] or [x, y, z], etc., the configuration information of the task degrees of freedom of the power mechanism 22 is included in the effective degrees of freedom of the robot arm 21, but is not completely matched, thus in controlling the power mechanism 22, only the [x, y, z, α] or [x, y, z] degrees of freedom can be adjusted, in this situation, the power mechanism 22 is constrained control, and the power mechanism 22 can be controlled within a predetermine range.

In particular, if the configuration information of the task degrees of freedom of the power mechanism 22 only includes [α, β], this belongs to the RCM constraint control of constraint controls, that is, moving around the remote moving center (i.e., the fixed point), only the yaw angle and the pitch angle can be adjusted, which can meet the fine tuning during the surgical process, which corresponds to the case associated with the second operation command above.

Of course, when the effective degrees of freedom information of the robot arm 21 includes [x, y, z, α, β, γ], by a configuration of the degrees of freedom of the power mechanism 22, the RCM constraint control can include adjustment of only the yaw angle, only the pitch angle, only the rolling angle, both the yaw angle and the pitch angle, both the yaw angle and the rolling angle, both the pitch angle and the rolling angle, and all of the yaw angle, the pitch angle and the rolling angle.

In step S16, specifically using the stiffness matrix, the six-dimensional force/torque vector of the external force can be analyzed to obtain the target position and/or pose information of the power mechanism at the base coordinate system of the robot arm.

In particular, the stiffness matrix is used to realize the conversion of the force information to the position and/or pose information, which is typically a matrix associated with the vector dimension of task degrees of freedom and external force. Exemplary, assuming that the configuration information of the task degrees of freedom of the power mechanism 22 describes a ($1 \leq a \leq 6$) degrees of freedom motion, and at the same time assumes that the vector dimension of the external force is b ($1 \leq b \leq 6$), the stiffness matrix is described as a matrix of a×b (row and column). Different stiffness matrices typically have different control parameters, which can be determined by finite experiments or computer auto-calculations.

The control parameter of the stiffness matrix can be set to be adjustable, to realize the linear or index enlarge or reduce of the external force information to the position and/or pose information according to need. Exemplary, an input device connected to the control device can be provided for inputting a control information for adjusting the control parameters of the stiffness matrix, wherein the control information is typically an input physical parameter, and the specific adjustment process can be achieved through the following steps:

Obtaining physical parameters.

In particular, the physical parameters may be discrete, or may be continuous, determined according to the characteristics of the input device itself, for example an input device such as a gear or button usually input discrete physical parameters, and input device types of stepless knob or touch screens usually input continuous physical parameters.

Combining with a parameter adjustment model and the physical parameters to adjust parameters in the stiffness matrix.

In an example, corresponding to discrete physical parameters, the parameter adjustment model can be a control parameter dictionary. This parameter dictionary stores multiple sets of control parameters, which one-to-one corresponds to a series of discrete physical parameters generated by the input device. In this situation, when the stiffness matrix is required to be controlled, by the mapping relationship between the physical parameters and the control parameters in the parameter dictionary, using the corresponding control parameter to adjust the stiffness matrix, thereby making it more adaptable for the operator's drag habits of the robotic arms and improve user experience.

In an example, corresponding to the continuous physical parameters, the parameter adjustment model can be a parameter calculation model. This parameter calculation model is a determined mathematical formula, a continuous physical parameter generated by the input device is configured as an independent variable in controlling the parameter computing model, and the control parameter is a dependent variable of the parameter calculation model and changed with the physical parameters input to the parameter calculation model. In this situation, when it is required to control the stiffness matrix, since the physical parameter and the control parameter have a relationship between the independent variable and dependent variable in controlling the parameter calculation model, the control parameter is calculated according to the physical parameters to adjust the stiffness matrix. In this embodiment, the parameter calculation model can be designed as a polynomial model, preferably a quintic polynomial model, because the quintic polynomial model has the incremental curve consistent in the slope direction, especially the trajectory of the quintic polynomial model is more flat at beginning section and end section, thus it is facilitated to smoothly deal with the external force.

The above parameter adjustment model can include the above both models to accommodate any control requirements; or may be taken from one of the above models, to accommodate a specific control requirement. The parameter adjustment model can be selected according to the type of the input device, and the control parameters can be acquired in conjunction with the physical parameters input by the input device.

In one embodiment, if the configuration information of the task degrees of the power mechanism 22 is partially included in the effective degrees of freedom information of the robot arm 21, a preferred option is prompting the configuration error, and another option is only allowing part of the degrees of freedom of the effective degrees of freedom of the robot arm 21 being adjustable. Take the robot arm 21 shown in FIG. 13 as an example, and if the configuration information of the task degrees of freedom of the power mechanism 22 is [y, z, α, γ, γ] or [x, y, z, α, β, γ], on one hand, it can be prompted configuration error, and on the other hand allowing degrees of freedom adjustable in [y, z, α, β] or [x, y, z, α, β]. This can be configured according to actual needs.

Figure 15:
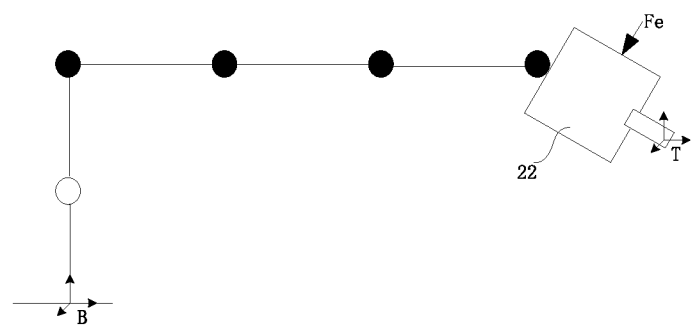
FIG. 15-FIG. 18 show different operating views of another configuration of the robot arm of FIG. 1.
Figure 19:
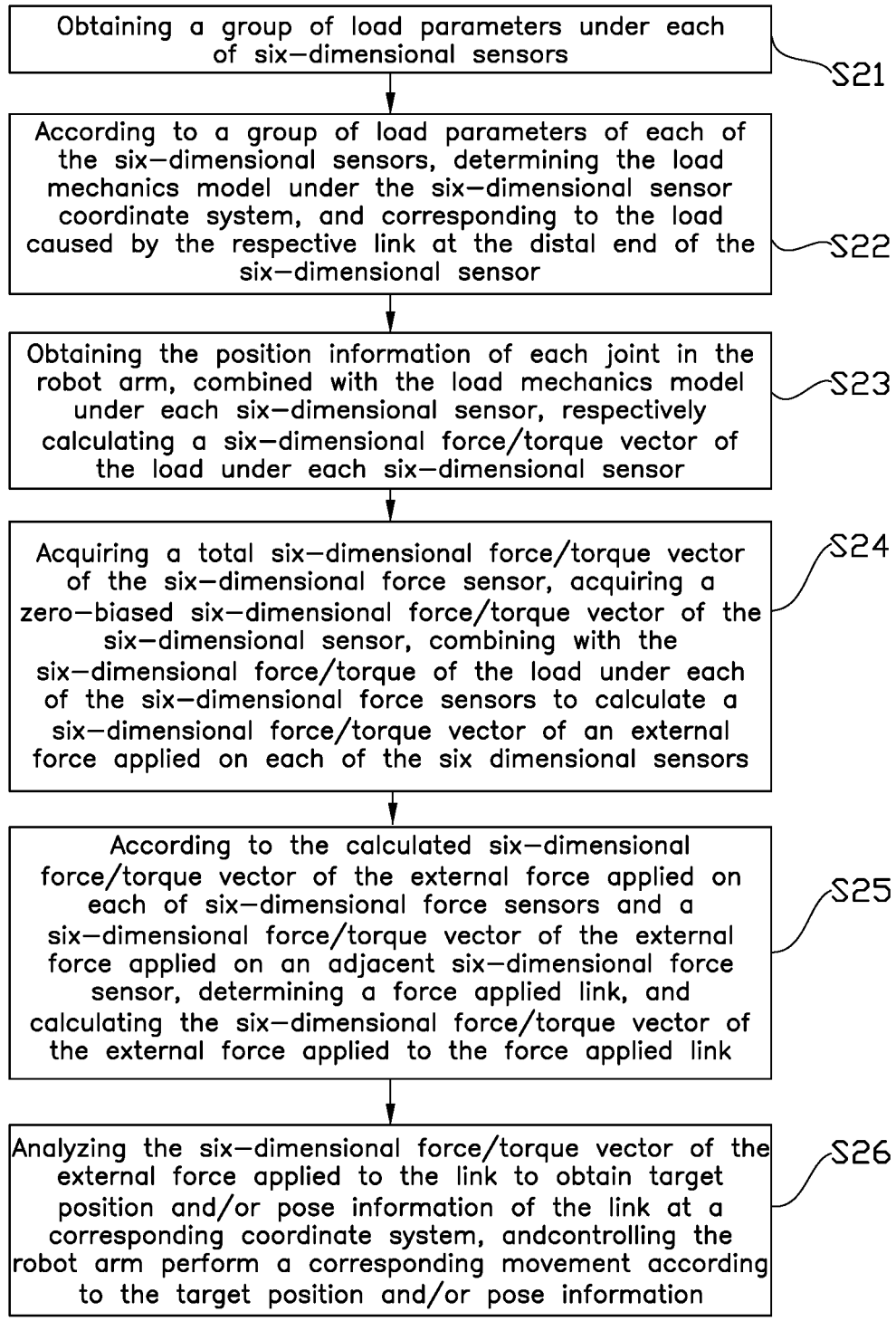
FIG. 19-FIG. 23 are flow charts of control methods according to various embodiments of the present disclosure.

The surgical robot can have another hardware configuration, mainly reflected in the number of six-dimensional sensor installation. In this embodiment, a six-dimensional sensor can be provided between two or more adjacent links including the power mechanism as one link, for example, as shown in FIG. 15, the same, the hollow circle "○" refers to the joint that does not have the six-dimensional sensor, and the solid round "●" refers to the joint that has installed the six-dimensional sensor. Through such hardware configurations, the operator can drag the links having the six-dimensional sensor other than the power mechanism, to achieve the corresponding control objects, especially for use in the case that there are redundant degrees of freedom of the robot arm. According to this hardware configuration, a control method of a robot arm in another surgical robot is provided, as shown in FIG. 19, the control method includes:

Step S21, obtaining a group of load parameters under each of six-dimensional sensors.

In particular, the group of load parameters includes load parameters of each link located at a distal end of the respective six-dimensional sensor. The load parameters include quality parameters and centroid parameters. It is worth noting that the load parameters of other links other than the power mechanism 22 can be obtained by measurement, and the load parameters of the power mechanism 22 can be obtained from steps S111 to S115 described in the foregoing embodiment, and will not be repeated herein.

Step S22, according to the group of load parameters of each of the six-dimensional sensors, determining a load mechanics model under a six-dimensional sensor coordinate system, and corresponding to a load caused by the respective link at the distal end of the six-dimensional sensor.

In particular, the expression form of load mechanics model under different six-dimensional sensor coordinate systems can be the same, but the expression content can be different. If the load mechanics model of the power mechanism under the six-dimensional sensor coordinate system is $F_m=f(S, P_{Load})$; the load mechanics model of a link adjacent to the power mechanism under the six-dimensional force sensor coordinate system is $F_m=f(S, P_{Load}, P_1)$, $P_1$ refers to the load parameters of the adjacent link, and $P_1$ is fixed while $P_{Load}$ may be changable; accordingly the load mechanics model in each six-dimensional sensor coordinate system can be obtained.

Step S23, obtaining position information of each joint in the robot arm, combined with the load mechanics model under each six-dimensional sensor, respectively calculating a six-dimensional force/torque vector of the load under each six-dimensional sensor.

Step S24, acquiring a total six-dimensional force/torque vector of the six-dimensional force sensor, acquiring a zero-biased six-dimensional force/torque vector of the six-dimensional sensor, combining with the six-dimensional force/torque of the load under each of the six-dimensional force sensors to calculate a six-dimensional force/torque vector of an external force applied on each of the six-dimensional sensors.

Step S25, according to the calculated six-dimensional force/torque vector of the external force applied on each of six-dimensional force sensors and a six-dimensional force/torque vector of the external force applied on an adjacent six-dimensional force sensor, determining a force applied link, and calculating a six-dimensional force/torque vector of the external force applied to the force applied link.

In particular, if the total six-dimensional force/torque vector at the corresponding six-dimensional sensor coordinate system is equal to the sum of the six-dimensional force/torque vector of the load at a distal end of the corresponding six-dimensional sensor, the zero-biased six-dimensional force/torque vector and the six-dimensional force/torque vector of an external force acted on an adjacent six-dimensional sensor, in this situation it can be determined that the link adjacent to the six-dimensional sensor does not have a force applied thereon. If the total six-dimensional force/torque vector in the corresponding six-dimensional sensor coordinate system is greater than the sum of the six-dimensional force/torque vector of the load at a distal end of the corresponding six-dimensional sensor, the zero-biased six-dimensional force/torque vector and the six-dimensional force/torque vector of an external force acted on an adjacent six-dimensional sensor, in this situation it can be determined that the link adjacent to the six-dimensional sensor have a force applied thereon, and the difference between the total six-dimensional force/torque vector and the sum of the above six-dimensional force/torque vectors is the six-dimensional force/torque vector of the external force applied on the force applied link. It is worth noting that "acted on" is different from "applied on", and the "acted on" includes "applied on".

In step S26, analyzing the six-dimensional force/torque vector of the external force applied to the link to obtain target position and/or pose information of the link at a corresponding coordinate system, and according to the target position and/or pose information, controlling the robot arm to perform a corresponding movement.

In this embodiment, the power mechanism can also be configured to configure the task degrees of freedom, and in step S26, combined with the target degrees of freedom of the power mechanism to analyze the six-dimensional/torque vector of the external force applied to the force applied link to obtain the target position and/or pose of the force applied link at the corresponding coordinate system. For this, it is no longer repeated.

Under the configuration of this example, in the links of the robotic arm 21, each of which has the six-dimensional sensor, one link can be the force applied link, or two or more of the links can be the force applied links:

In an embodiment, when the number of the force applied link is one, if the force applied link is a power mechanism, as shown in FIG. 15, in step S26, the control method includes:

Combining with the target degrees of freedom of the power mechanism to analyze the six-dimensional force/torque vector of the external force of the power mechanism, obtaining the target position and/or pose information of the power mechanism at the base coordinate system of the robot arm.

According to the target position and/or pose information to control the links of the robot arm to move, thereby the power mechanism reaching the corresponding target position and/or pose.

This situation is consistent with the example shown in FIG. 8, such as under the configuration of FIG. 8, the power mechanism 22 can also be freely dragged or be dragged in RCM constraint control, that is, no matter the input is the first operating command or the second operating command, can be controlled according to the above steps.

Figure 16:
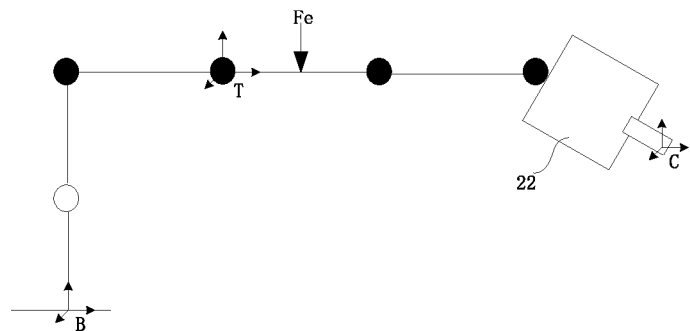

In an embodiment, when the force applied link is only one, if the force applied link is not the power mechanism and the acquired is the first operating command input, as shown in FIG. 16, in the above step S26, including:

Analyzing the six-dimensional force/torque vector of the external force applied on the link to obtain the target position and/or pose information of the force applied link at the base coordinate system of the robot arm.

According to the target position and/or pose information, controlling a movement of the force applied link of the robot arm and each link at a proximal end of the force applied link to allow the force applied link to move to the corresponding target position and/or pose.

In this situation, the robot arm 21 is divided into two segments, and controls each of the links at the proximal end of the force applied link to reach the corresponding target position and/or pose, and each of the links at the distal end of the force applied link move with the force applied link.

Figure 20:
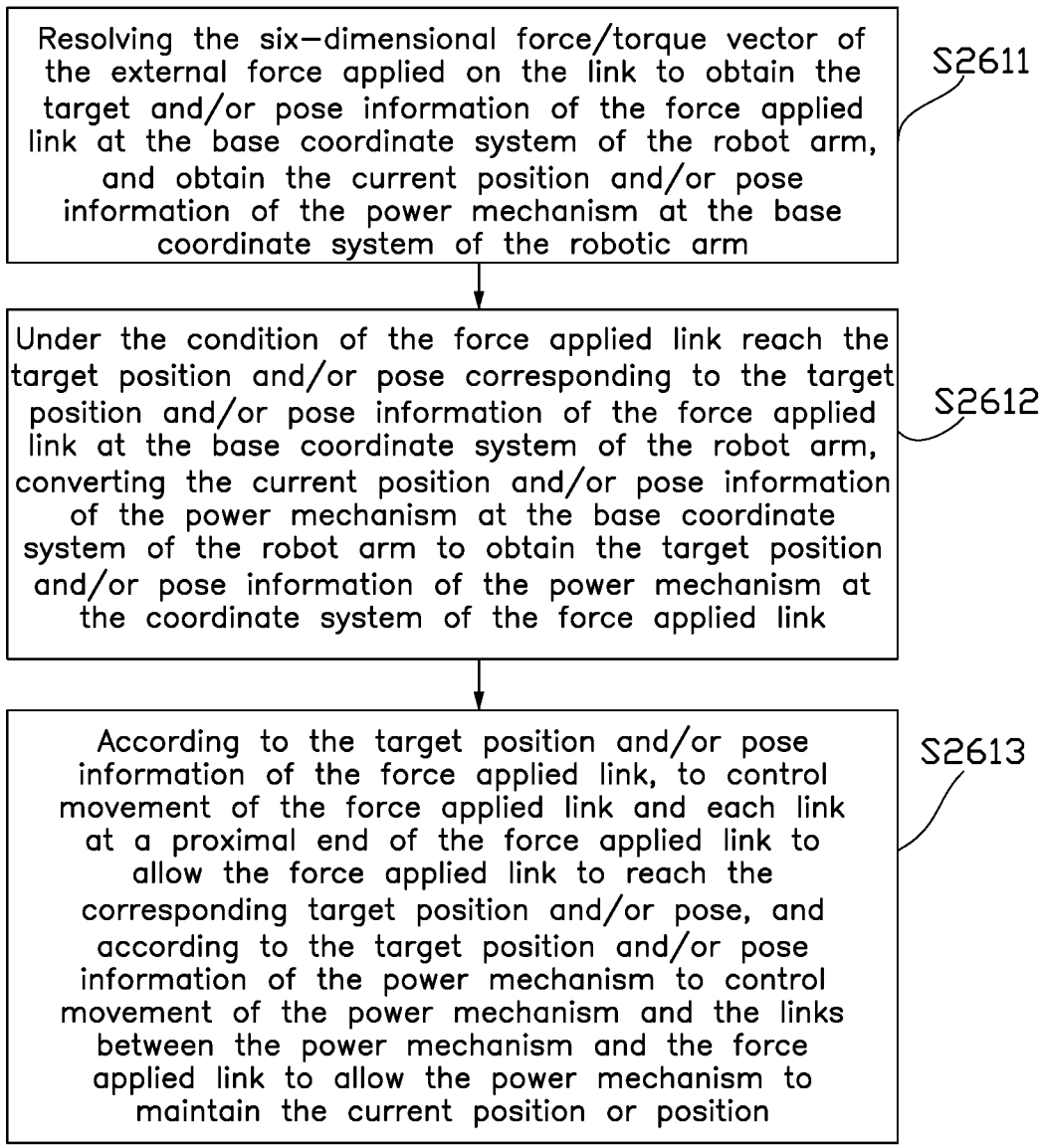

In an embodiment, when the number of the force applied link is one, if the force applied link is not the power mechanism and the acquired input is the aforementioned second operating command, combined with FIGS. 16 and 20, in the above step S26, the control method includes:

Step S2611, analyzing the six-dimensional force/torque vector of the external force applied on the link to obtain the target and/or pose information of the force applied link at the base coordinate system of the robot arm, and obtaining the current position and/or pose information of the power mechanism at the base coordinate system of the robotic arm.

Step S2612, under a condition of the force applied link reaching the target position and/or pose corresponding to the target position and/or pose information of the force applied link at the base coordinate system of the robot arm, converting the current position and/or pose information of the power mechanism at the base coordinate system of the robot arm to obtain the target position and/or pose information of the power mechanism at the coordinate system of the force applied link.

In step S2612, the target position and/or pose information of the power mechanism at the coordinate system of the force applied link can be calculated using the formula $^T_C T = ^B_T T^{-1} \cdot ^B_C T$. In particular, $^T_C T$ refers to the target position and/or pose information of the power mechanism at the coordinate system of the force applied link, $^B_T T^{-1}$ refers to the target position and/or pose information of the force applied link at the base coordinate system of the robot arm, $^B_C T$ refers to the current position and/or pose information of the force applied link at the base coordinate system of the robot arm, B refers to the base coordinate system of the robot arm, and T refers to the coordinate system of the force applied link.

Step S2613, according to the target position and/or pose information of the force applied link, controlling a movement of the force applied link and each link at a proximal end of the force applied link to allow the force applied link to reach the corresponding target position and/or pose, and according to the target position and/or pose information of the power mechanism, controlling a movement of the power mechanism and the links between the power mechanism and the force applied link to allow the power mechanism to maintain the current position or pose.

In this situation, the robot arm 21 is divided into two segments, controls each of the links at the proximal end of the force applied link to reach the corresponding target position and/or pose, and controls each of the links at the distal ends of the force applied link to move to allow the power mechanism 22 maintain its current position and/or pose. The usage scenario can be a certain movement of a section of the robot arm to achieve avoidance, while ensuring the safety of the surgical procedure.

Prior to the above step S2613, the effectiveness of the target position and/or pose information of the power mechanism at the coordinate system of the force applied link can be determined, and step S2613 is performed if it is effective. For example, the step of determining the effectiveness can be performed in this way: the target position and/or pose information is analyzed into a target motion state parameter (including positional parameters, speed parameters, and acceleration parameters) of each of the joints of a section of the robot arm, then the target motion parameter is compared with the motion state threshold of the corresponding joint, if each target motion parameter is within the corresponding motion state threshold, it is determined effective, otherwise, it is determined ineffective.

Figure 21:
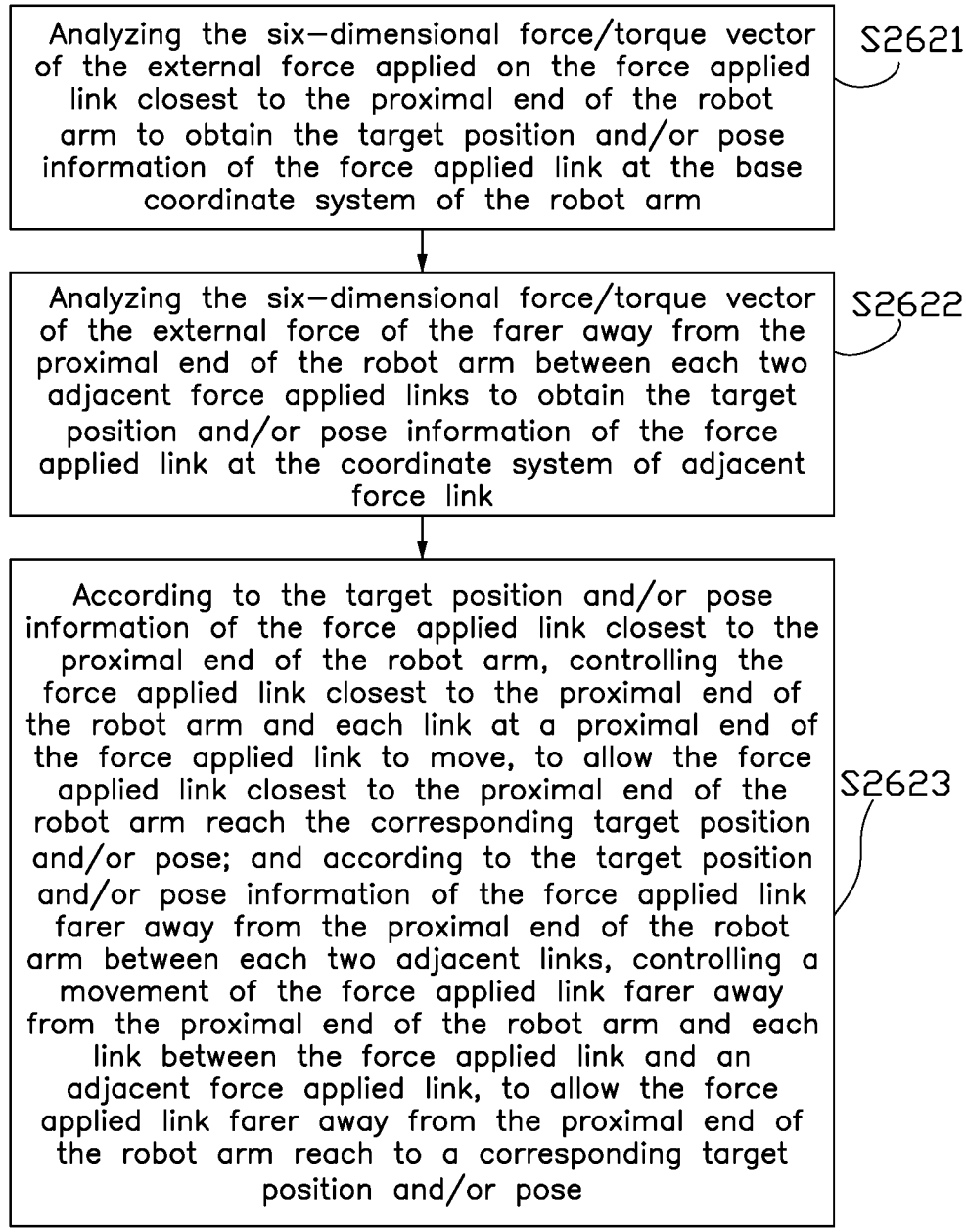

In an embodiment, when the force applied link is more than two, if the acquired input is the above described first operating command, as shown in FIG. 21, in the above step S26, the control method includes:

Step S2621, analyzing the six-dimensional force/torque vector of the external force applied on the force applied link closest to the proximal end of the robot arm to obtain the target position and/or pose information of the force applied link at the base coordinate system of the robot arm.

Step S2622, analyzing the six-dimensional force/torque vector of the external force of the farer away from the proximal end of the robot arm between each two adjacent force applied links to obtain the target position and/or pose information of the force applied link at the coordinate system of adjacent force link.

Step S2623, according to the target position and/or pose information of the force applied link closest to the proximal end of the robot arm, controlling the force applied link closest to the proximal end of the robot arm and each link at a proximal end of the force applied link to move, to allow the force applied link closest to the proximal end of the robot arm reach the corresponding target position and/or pose; and according to the target position and/or pose information of the force applied link farer away from the proximal end of the robot arm between each two adjacent links, controlling a movement of the force applied link farer away from the proximal end of the robot arm and each link between the force applied link and an adjacent force applied link, to allow the force applied link farer away from the proximal end of the robot arm reach to a corresponding target position and/or pose.

In this case, if the number of force applied links is d, it is equivalent to divide the robot arm 21 into d+1 segments, except that the force applied link closest to the proximal end of the robot arm moves according to the corresponding target position and/or pose information to reach the target position and/or pose at the base coordinate system of the robot arm, the remaining force applied links move according to the respective target position and/or pose information, thereby the corresponding force applied link move relative to the coordinate system of the force applied link adjacent to a proximal end thereof to reach corresponding target position and/or pose. If a distal end of the force applied link at the remote end of the robot arm 21 also has links, these links can be moved with the force applied link at the remote end of the robot arm 21.

Figure 17:
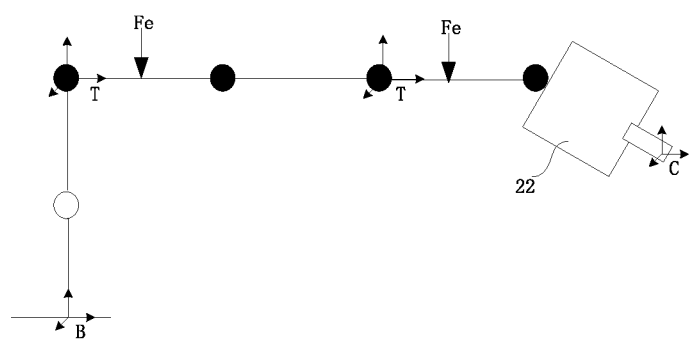
Figure 18:
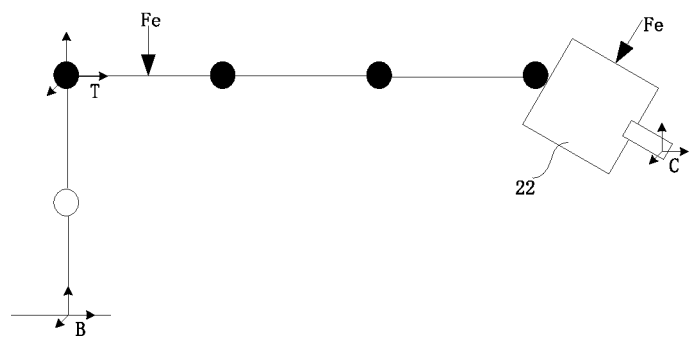

Steps S2621 to S2623 are suitable for any of FIGS. 17 and 18, i.e., regardless of whether or not the force applied link includes the power mechanism 22.

Figure 22:
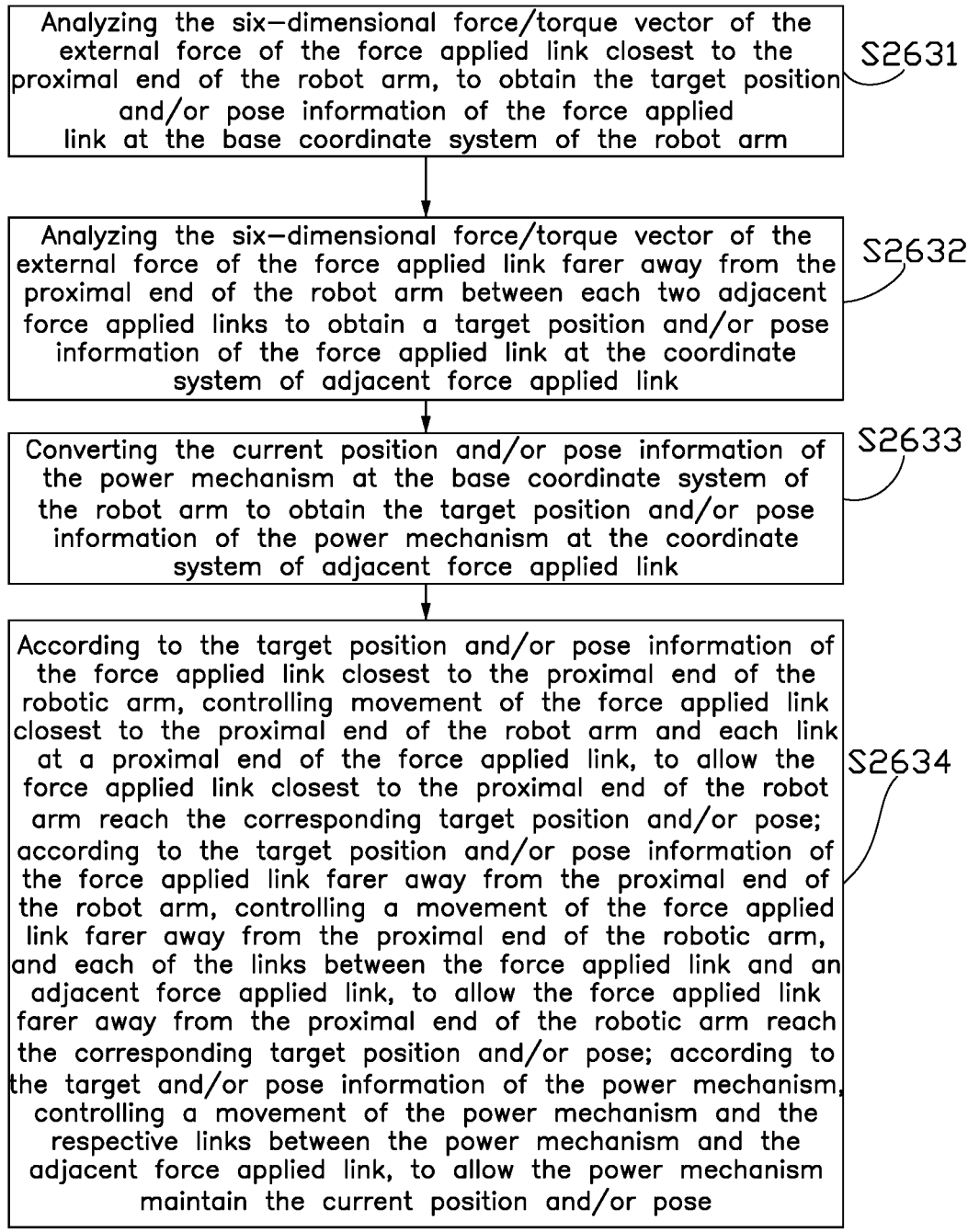

In an embodiment, if the number of the force applied links is more than two, if the acquired input is the above described second operating command, and the force applied links do not include the power mechanism, in connection with FIGS. 17 and 22, the above steps S26, including:

Step S2631, analyzing the six-dimensional force/torque vector of the external force of the force applied link closest to the proximal end of the robot arm, to obtain the target position and/or pose information of the force applied link at the base coordinate system of the robot arm.

Step S2632, analyzing the six-dimensional force/torque vector of the external force of the force applied link farer away from the proximal end of the robot arm between each two adjacent force applied links to obtain a target position and/or pose information of the force applied link at the coordinate system of adjacent force applied link.

Step S2633, acquiring the current position and/or pose information of the power mechanism information at the base system of the robot arm, and under the condition of the force applied link reaching the target position and/or pose corresponding to the target position and/or pose information at the corresponding coordinate system, converting the current position and/or pose information of the power mechanism at the base coordinate system of the robot arm to obtain the target position and/or pose information of the power mechanism at the coordinate system of adjacent force applied link.

Step S2633 can also be converted using the formulas and principles in step S2612.

Step S2634, according to the target position and/or pose information of the force applied link closest to the proximal end of the robotic arm, controlling a movement of the force applied link closest to the proximal end of the robot arm and each link at a proximal end of the force applied link, to allow the force applied link closest to the proximal end of the robot arm reach the corresponding target position and/or pose. According to the target position and/or pose information of the force applied link farer away from the proximal end of the robot arm, controlling a movement of the force applied link farer away from the proximal end of the robotic arm, and each of the links between the force applied link and an adjacent force applied link, to allow the force applied link farer away from the proximal end of the robotic arm reach the corresponding target position and/or pose. According to the target and/or pose information of the power mechanism, controlling a movement of the power mechanism and the respective links between the power mechanism and the adjacent force applied link, to allow the power mechanism maintain the current position and/or pose.

In this situation, the robot arm 21 is also equivalent to a multi-segment, each of force applied links moves to the target position and/or pose relative to the respective coordinate system, while maintaining the power mechanism 22 the current position and/or pose to ensure the operation of the operation safety.

Figure 23:
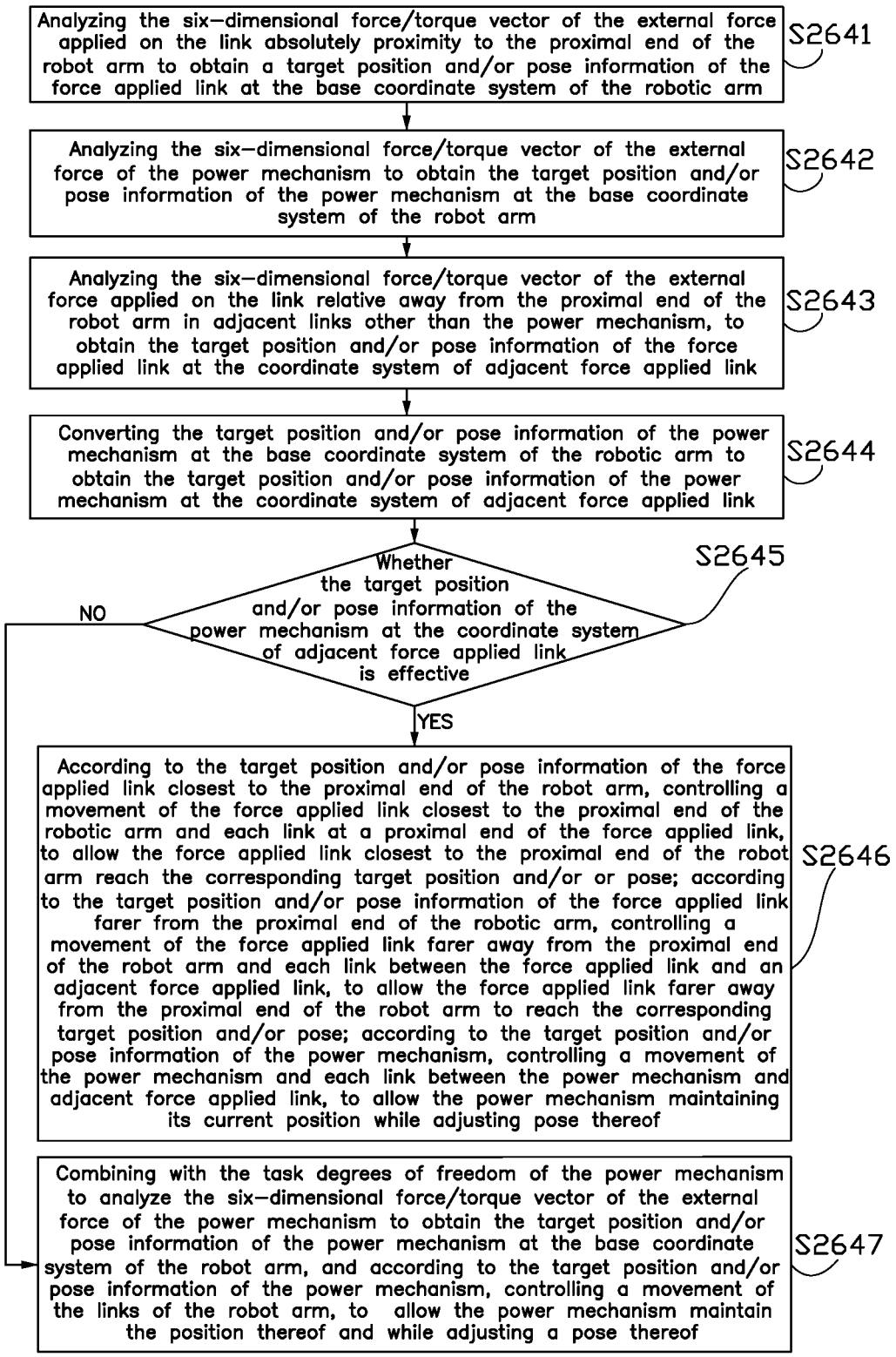

In one embodiment, if the number of the force applied links is more than two or more, if the previously described second operating command is acquired, the power mechanism is included in the force applied links, in conjunction with FIGS. 18 and 23, the above step S26 including:

Step S2641, analyzing the six-dimensional force/torque vector of the external force applied on the link absolutely proximity to the proximal end of the robot arm to obtain a target position and/or pose information of the force applied link at the base coordinate system of the robotic arm.

Step S2642, analyzing the six-dimensional force/torque vector of the external force of the power mechanism to obtain the target position and/or pose information of the power mechanism at the base coordinate system of the robot arm.

Step S2643, analyzing the six-dimensional force/torque vector of the external force applied on the link relative away from the proximal end of the robot arm in adjacent links other than the power mechanism, to obtain the target position and/or pose information of the force applied link at the coordinate system of adjacent force applied link.

Step S2644, under the condition of the force applied link adjacent to the power mechanism reaching the target position and/or pose corresponding to the target position and/or pose information at the corresponding coordinate system, converting the target position and/or pose information of the power mechanism at the base coordinate system of the robotic arm to obtain the target position and/or pose information of the power mechanism at the coordinate system of adjacent force applied link.

Step S2644 may also be converted using the formula and principle as in step S262.

Step S2645, determining whether the target position and/or pose information of the power mechanism at the coordinate system of adjacent force applied link is effective.

If it is effective, the process proceeds to step S2646. If it is ineffective, the process proceeds to step S2647.

Step S2646, according to the target position and/or pose information of the force applied link closest to the proximal end of the robot arm, controlling a movement of the force applied link closest to the proximal end of the robotic arm and each link at a proximal end of the force applied link, to allow the force applied link closest to the proximal end of the robot arm reach the corresponding target position and/or or pose. According to the target position and/or pose information of the force applied link farer from the proximal end of the robotic arm, controlling a movement of the force applied link farer away from the proximal end of the robot arm and each link between the force applied link and an adjacent force applied link, to allow the force applied link farer away from the proximal end of the robot arm to reach the corresponding target position and/or pose. According to the target position and/or pose information of the power mechanism, controlling a movement of the power mechanism and each link between the power mechanism and adjacent force applied link, to allow the power mechanism maintaining its current position while adjusting pose thereof.

Step S2647, combining with the task degrees of freedom of the power mechanism to analyze the six-dimensional force/torque vector of the external force of the power mechanism to obtain the target position and/or pose information of the power mechanism at the base coordinate system of the robot arm, and according to the target position and/or pose information of the power mechanism, controlling a movement of the links of the robot arm, to allow the power mechanism maintain the position thereof and while adjusting a pose thereof.

In this situation, that is when the target position and/or pose information determined in step S2645 is effective, the robot arm 21 performs segmentation control and realizes the RCM constraint drag control of the power mechanism 22; when it is ineffective, the robot arm 21 is performed overall control to realize the RCM constraint drag control.

In the above embodiment, the validity of the acquired target position and/or pose information can be determined, the determination process and the principle are the same or similar to the judgment procedure between step S2612 and step S2613, and enter the corresponding subsequent steps implement the corresponding control, and will not be described here.

The above embodiment is suitable for controlling a robot arm in a surgical robot as shown in FIG. 1. The type of surgical robot includes a robot arm 21 and an operating arm 31 having an end instrument 34 at the distal end of the robot arm 21, which has several degrees of freedom.

Figure 24:
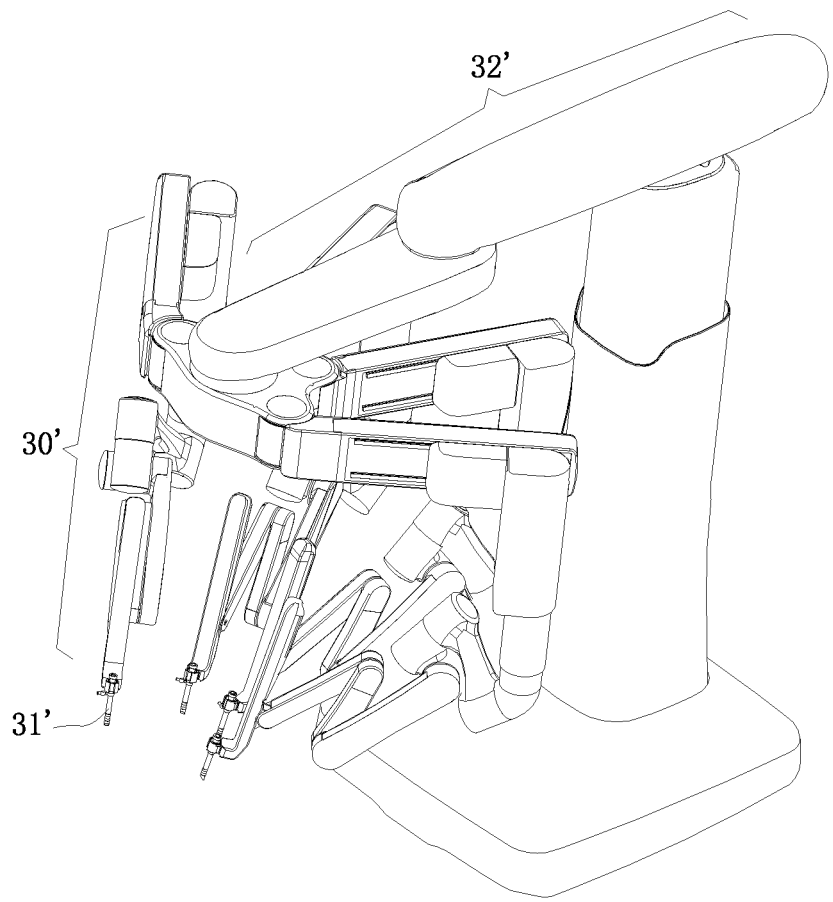
FIG. 24 is a schematic structural view of a surgical robot according to another embodiment of the present disclosure.

The above embodiments are also applicable to control of end instruments in the surgical robot type shown in FIG. 24. This type of surgical robot includes a main arm 32', one or more adjustment arms 30' mounted at a remote end of the main arm 32', and one or more operating arms 31' each having an end instrument, with the main arm 32', the adjustment arm 30' and the operating arm 31' each have several degrees of freedom. As shown in FIG. 24, in the surgical robot, there may be four adjustment arms 30', and each of the adjusting arms 30' can have only one operating arm 31'. According to the actual use scenario, the three-section arm structure of the surgical robot as shown in FIG. 24 can be configured to be the two-section arm structure of the surgical robot type shown in FIG. 1 to achieve control. In an embodiment, in the case where the concept of the operating arms in the two types of surgical robots is consistent, for example, according to the configuration, each adjustment arm 30' in the surgical robot of the type shown in FIG. 24 can be regarded as the robot arm 21 in the surgical robot type shown in FIG. 1 to perform control; another example, according to the configuration, any of the adjustment arms 30' and the main arm 32' as an entire in the surgical robot type shown in FIG. 24 can be regarded to be the robot arm 21 in the surgical robot type shown in FIG. 1 to achieve control. In an embodiment, the main arm 32' in the surgical robot type shown in FIG. 24 can be considered as a robot arm 21 in the surgical robot type shown in FIG. 24. The adjustment arm 30' and its corresponding operating arm 31' as an entire in the surgical robot type shown in FIG. 24 can be regarded to be the operating arm 31 in the surgical robot type shown in FIG. 1 to achieve control.

In an embodiment, the control method of the above-mentioned surgical robot is generally configured to be implemented in the control device of the surgical robot, the control device includes a memory and more than one processor, the memory is configured for storing a computer program, a processor is configured for loading and executing the computer program to carry out the control method described in any of the above embodiments.

In an embodiment, a computer readable storage medium is provided, and a computer readable storage medium stores a computer program, which is configured to perform the control method steps described in any of the above-described embodiments.

The various technical features of the above-described embodiments may be combined in any combination, so that the description is concise, and all possible combinations of the various technical features in the above-described embodiments are described. However, as long as the combination of these technical features does not conflict, it is to be understood that the scope of the present specification is not to be taken in a limiting sense.

The above-described embodiments have only expressed several embodiments of the present application, which are described in more detail and detail, but are not therefore to be construed as limiting the scope of the present application. It should be noted that variations and modifications may be made to one of ordinary skill in the art without departing from the spirit of the present application, all of which fall within the scope of the present application. Therefore, the scope of the appended claims should be accorded the broadest interpretation so as to encompass all such modifications and similar arrangements.

What is claimed is:

1. A surgical robot, comprising:
a robot arm comprising a plurality of links connected by joints, and one of the plurality of links at a remote end of the robot arm being configured as a power mechanism; and
a control device coupled with the robot arm, the control device being configured for:
acquiring an external force applied on the power mechanism;
acquiring an input operating command associated with task degrees of freedom of the power mechanism; and
combining the task degrees of freedom of the power mechanism to analyze the external force to acquiring target position and/or pose information of the power mechanism at a base coordinate system of the robot arm, and according to the target position and/or pose information, controlling a movement of each of the joints of the robot arm to allow the power mechanism to move within the task degrees of freedom to reach a corresponding target position and/or pose;
wherein the operating command comprises a first operating command and a second operating command;
the first operating command is associated with a case that the task degrees of freedom are completely matched with effective degrees of freedom of the robot arm, and the acquired target position and/or pose information analyzed according to the first operating command allows a free drag control of the power mechanism;
the second operating command is associated with a case that the task degrees of freedom are not completely matched with the effective degrees of freedom of the robot arm, but included in the effective degrees of freedom of the robot arm, and the acquired target position and/or pose analyzed according to the second operating command allows a drag control of the power mechanism within a predetermined task degree of freedom.

2. The surgical robot of claim 1, wherein the second operating command is associated with a case of the task degrees of freedom of the power mechanism being selected from effective degrees of freedom which is within the effective degrees of freedom of the robot arm and associated with pose degrees of freedom thereof.

3. The surgical robot of claim 1, wherein a six-dimensional force sensor is disposed between the power mechanism and an adjacent link, for coupling with the control device and for acquiring the external force, the power mechanism comprises rails and a power unit slidable on each of the rails, and the power unit is configured for mounting and driving an operating arm for surgical operation,
    wherein, in the step of acquiring the external force applied on the power mechanism, the control device is configured to perform:
    according to installation state information and position state information inside of the power mechanism, acquiring load parameters of the power mechanism at a corresponding state, the load parameters comprise a quality parameter and a centroid parameter;
    according to the load parameters, determining a load mechanics model corresponding to a load caused by the power mechanism at a coordinate system of the six-dimensional force sensor;
    acquiring position information of each of the plurality of links of the robot arm, and calculating a six-dimensional force/torque vector of the load according to the load mechanics model;
    acquiring a zero-biased six-dimensional force/torque vector of the six-dimensional force sensor and a total six-dimensional force/torque vector; and
    according to the total six-dimensional force/torque vector, the zero-biased six-dimensional force/torque vector, and the six-dimensional force/torque vector of the load, calculating a six-dimensional force/torque vector of the external force applied on the power mechanism,
    wherein, the step of combining the task degrees of freedom of the power mechanism to analyze the external force to acquire target position and/or pose information of the power mechanism at the base coordinate system of the robot arm, comprises:
    combining the task degrees of freedom to analyze the six-dimensional force/torque vector of the external force to obtain the target position and/or pose information of the power mechanism at the base coordinate system of the robot arm.

4. The surgical robot of claim 3, wherein the installation state information is associated with an installation state of the operating arm at each of the power units, the position state information is associated with a position state of each of the power units relative to a corresponding rail, the installation state information comprises information as to whether the power unit has installed the operating arm, and/or type information of the operating arm installed on the power unit,
    wherein, before the step of according to the installation state information and the position state information inside of the power mechanism, acquiring the load parameters of the power mechanism at the corresponding state, the control device is configured to perform:
    based on each of the installation state of the power mechanism, detecting the load parameters of the power mechanism at a corresponding installation state and different internal position states; and
    according to the detected load parameters of the power mechanism at the corresponding installation state and the different internal position states, establishing a parameter calculating model corresponding to each of the installation state of the power mechanism;
    wherein, the step of according to the installation state information and the position state information inside of the power mechanism, acquiring the load parameters of the power mechanism at the corresponding state, comprises:
    acquiring the installation state information and the position state information inside of the power mechanism;
    selecting the parameter calculating model according to the installation state of the power mechanism; and
    based on the selected parameter calculating model and the position state information of the power mechanism, calculating the load parameters of the power mechanism at the corresponding states.

5. The surgical robot of claim 1, wherein, in the step of analyzing the external force to acquire the target position and/or pose information of the power mechanism at the base coordinate system of the robot arm, the control device is configured to perform:
    by controlling a parameter adjustable stiffness matrix, converting the external force to the target position and/or pose information of the power mechanism at the base coordinate system of the robot arm.

6. A surgical robot, comprising:
    a robot arm comprising a plurality of links connected by joints, and one of the plurality of links at a remote end of the robot arm being configured as a power mechanism; and
    a control device coupled with the robot arm, the control device being configured for:
    determining a force applied link from the plurality of links and acquiring an external force applied on the force applied link;
    acquiring an input operating command associated with task degrees of freedom of the power mechanism; and
    combining the task degrees of freedom of the power mechanism to analyze the external force applied on the force applied link to acquire target position and/or pose information of the force applied link at a corresponding coordinate system, and according to the target position and/or pose information, controlling a movement of the robot arm;
    wherein the operating command comprises a first operating command and a second operating command;
    the first operating command is associated with a case that the task degrees of freedom are completely matched with effective degrees of freedom of the robot arm, and according to the first operating command to analyze the acquired target position and/or pose information to allow a free drag control of the power mechanism;
    the second operating command is associated with a case that the task degrees of freedom are not completely matched with the effective degrees of freedom of the robot arm, but included in the effective degrees of freedom of the robot arm, and according to the second operating command to analyze the acquired target position and/or pose information to allow a drag control of the power mechanism within a predetermined task degrees of freedom.

7. The surgical robot of claim 6, wherein the second operating command is associated with a case of the task degrees of freedom of the power mechanism being selected from effective degrees of freedom which is within the effective degrees of freedom of the robot arm and associated with pose degrees of freedom thereof.

8. The surgical robot of claim 6, wherein a six-dimensional force sensor is disposed between two or more adjacent links including the power mechanism, for coupling with the control device and for acquiring the external force, the power mechanism comprises rails and a power unit slidable on each of the rails, and the power unit is configured for installing and driving an operating arm for surgical operation;

wherein, in the step of determining the force applied link from the plurality of links and acquiring the external force applied on the force applied link, the control device is configured to perform:

acquiring a group of load parameters of each of the six-dimensional force sensor, the group of load parameters comprising load parameters of each of the plurality of links located at a remote end of a corresponding six-dimensional force sensor, wherein the load parameters of the power mechanism are acquired according to installation state information and position state information inside of the power mechanism, the load parameters comprise a quality parameter and a centroid parameter;

according to the group of load parameters, determining a load mechanics model corresponding to a load caused by the plurality of links located at a remote end of the six-dimensional force sensor at a coordinate system of the six-dimensional force sensor;

acquiring position information of each of joints of the robot arm, and combining the load mechanics model of each of the six-dimensional force sensor to calculate a six-dimensional force/torque vector of the load of each of the six-dimensional force sensor;

acquiring a zero-biased six-dimensional force/torque vector and a total six-dimensional force/torque vector, combined with the six-dimensional force/torque of the load of each of the six-dimensional force sensors to calculate a six-dimensional force/torque vector of an external force applied on each of the six-dimensional force sensor; and according to the calculated six-dimensional force/torque vector of the external force applied on each of the six-dimensional force sensor and a six-dimensional force/torque vector of an external force applied on an adjacent six-dimensional force sensor at a remote end of each of the six-dimensional force sensor, determining the force applied link, and calculating a six-dimensional force/torque vector of the external force applied on the force applied link, wherein, the step of combining the task degrees of freedom of the power mechanism to analyze the external force applied on the force applied link to acquire the target position and/or pose information of the force applied link at the corresponding coordinate system, comprises:

combining with the task degrees of freedom of the power mechanism to analyze the six-dimensional force/torque vector of the external force applied on the force applied link to acquire the target position and/or pose information of the force applied link at the corresponding coordinate system.

9. The surgical robot of claim 8, wherein the installation state information is associated with an installation state of the operating arm on each of the power units, the position state information is associated with a position state of the power unit relative to the rail, the installation state information comprises information as to whether the power unit has installed the operating arm, and/or type information of the operating arm installed on the power unit, wherein, before the step of according to the installation state information and the position state information inside of the power mechanism, acquiring the load parameters of the power mechanism at the corresponding state, the control device is configured to perform:

based on each of the installation state of the power mechanism, respectively determining the load parameters of the power mechanism at a corresponding installation state and different internal position states; and according to the determined load parameters of the power mechanism at the corresponding installation state and the different internal position states, establishing a parameter calculation model corresponding to each of the installation state of the power mechanism;

wherein, the step of according to the installation state information and position state information of the power mechanism, acquiring the load parameters of the power mechanism at the corresponding state, comprises:

acquiring the installation state information and the position state information of the power mechanism;

according to the installation state information of the power mechanism, selecting a parameter calculation model;

based on the selected parameter calculation model and the position state information of the power mechanism to calculate the load parameters of the power mechanism at the corresponding state.

10. The surgical robot of claim 6, wherein, in the step of analyzing the external force applied on the force applied link to acquire the target position information of the force applied link at the corresponding coordinate system of the robot arm, the control device is configured to perform:

using a parameter adjustable stiffness matrix converting the external force applied on the force applied link to the target position and/or pose information of the power mechanism at a base coordinate system of the robot arm.

11. The surgical robot of claim 6, wherein in a situation of the number of the force applied link is one, if the force applied link is the power mechanism, in the step of the control device being configured for analyzing the external force applied on the force applied link to acquire the target position and/or pose information of the force applied link at the corresponding coordinate system, and according to the target position and/or pose information, controlling a movement of the robot arm, the control device is configured to perform:

combining the task degrees of freedom of the power mechanism to analyze the external force applied on the force applied link to acquire the target position and/or pose information of the power mechanism at a base coordinate system of the robot arm; and according to the target position and/or pose information, controlling a movement of each of the plurality of links of the robot arm to allow the power mechanism to reach a corresponding target position and/or pose.

12. The surgical robot of claim 6, wherein in a situation of the number of the force applied link is one, if the force applied link is not the power mechanism and an acquired input is the first operating command, in the step of analyzing the external force applied on the force applied link to acquire the target position and/or pose information of the force applied link at the corresponding coordinate system, and according to the target position and/or pose information, controlling the movement of the robot arm, the control device is configured to perform:

analyzing the external force applied on the force applied link to acquire the target position and/or pose information of the force applied link at a base coordinate system of the robot arm; and according to the target position and/or pose information, controlling a movement of the force applied link and each of the plurality of links at a proximal end of the force applied link to allow the force applied link to reach a corresponding target position and/or pose.

13. The surgical robot of claim 6, wherein in a situation of the number of the force applied link is one, if the force applied link is not the power mechanism and an acquired input is the second operating command, in step of analyzing the external force applied on the force applied link to acquire the target position and/or pose information of the force applied link at the corresponding coordinate system, and according to the target position and/or pose information, controlling the movement of the robot arm, the control device is configured to perform:

analyzing the external force applied on the force applied link to acquire the target position and/or pose information of the force applied link at a base coordinate system of the robot arm, and acquiring current position and/or pose information of the power mechanism at the base coordinate system of the robot arm;

converting the current position and/or pose information of the power mechanism at the base coordinate system of the robot arm to obtain the target position and/or pose information of the power mechanism at a coordinate system of the force applied link and at when the force applied link reaches a target position and/or pose corresponding to the target position and/or pose information of the force applied link at the base coordinate system of the robot arm; and according to the target position and/or pose information of the force applied link, controlling a movement of the force applied link and each of the plurality of links at a proximal end of the force applied link to allow the force applied link to reach a target position and/or pose, and according to the target position and/or pose information of the power mechanism, controlling a movement of the plurality of links between the power mechanism and the force applied link to allow the power mechanism to maintain a current position and/or pose.

14. The surgical robot of claim 6, wherein in a situation of the number of the force applied link is two or more, if an acquired input is the first operating command, in step of analyzing the external force applied on the force applied link to acquire the target position and/or information of the force applied link at a corresponding coordinate system, and according to the target position and/or pose information, controlling a movement of the robot arm, the control device is configured to perform:

analyzing the external force applied on the force applied link closest to a proximal end of robot arm to acquire the target position and/or pose information of the force applied link at a base coordinate system of the robot arm;

analyzing the external force applied on the force applied link farer away from the proximal end of the robot arm between each two adjacent force applied links to obtain the target position and/or pose information of the force applied link at the coordinate system of adjacent force applied link;

according to the target position and/or pose information of the force applied link closest to the proximal end of robot arm, controlling a movement of the force applied link closest to the proximal end of robot arm and adjacent links to allow the force applied link closest to the proximal end of robot arm to reach the target position and/or pose; and according to the target position and/or pose information of the force applied link farer away from the proximal end of the robot arm between two adjacent links, controlling a movement of the links between the force applied link farer away the proximal end of the robot arm and the adjacent force applied link to allow the force applied link farer away the proximal end of the robot arm to reach a corresponding target position and/or pose.

15. The surgical robot of claim 6, wherein in a situation of the number of the force applied link is two or more, if an acquired input is the second operating command and the force applied links do not include the power mechanism, in step of analyzing the external force applied on the force applied link to acquire the target position and/or information of the force applied link at the corresponding coordinate system, and according to the target position and/or pose information, controlling a movement of the robot arm, the control device is configured to perform:

analyzing the external force applied on the force applied link closest to a proximal end of robot arm to acquire the target position and/or pose information of the force applied link at a base coordinate system of the robot arm;

analyzing the external force applied on the force applied link farer away from the proximal end of the robot arm between each two adjacent force applied links to obtain the target position and/or pose information of the force applied link at the coordinate system of adjacent force applied link;

acquiring current position and/or pose information of the power mechanism at the base coordinate system of the robot arm, converting the current position and/or pose information of the power mechanism at the base coordinate system of the robot arm to obtain the target position and/or pose information of the power mechanism at the coordinate system of adjacent force applied link and at when the force applied links reach the target position and/or pose corresponding to the target position and/or pose information at the respective coordinate systems;

according to the target position and/or pose information of the force applied link closest to the proximal end of robot arm, controlling a movement of the force applied link closest to the proximal end of robot arm and the each link at the proximal end of the force applied link to allow the force applied link closest to the proximal end of robot arm reach the target position and/or pose; according to the target position and/or pose information of the force applied link farer away from the proximal end of the robot arm, controlling a movement of the force applied link farer away from the proximal end of the robot arm and the links between the force applied link and an adjacent force applied link to allow the force applied link farer away the proximal end of the robot arm to reach a corresponding position and/or pose; and according to target position and/or pose information of the power mechanism, controlling a movement of the power mechanism and the links between the power mechanism and the adjacent force applied link to allow the power mechanism to maintain the current position and/or pose.

16. The surgical robot of claim 6, wherein in a situation of the number of the force applied link is two or more, if an acquired input is the second operating command and the power mechanism is not included in the force applied links, in step of analyzing the external force applied on the force applied link to acquire the target position and/or information of the force applied link at the corresponding coordinate system, and according to the target position and/or pose information, controlling a movement of the robot arm, the control device is configured to perform:

analyzing the external force applied on the force applied link closest to a proximal end of robot arm to acquire the target position and/or pose information of the force applied link at a base coordinate system of the robot arm;

analyzing the external force of the power mechanism to obtain the target position and/or pose information of the power mechanism at the base coordinate system of the robot arm;

analyzing the external force applied on the force applied link farer away from the proximal end of the robot arm between each two adjacent force applied links except the power mechanism to obtain the target position and/or pose information of the force applied link at the coordinate system of adjacent force applied link;

converting the current position and/or pose information of the power mechanism at the base coordinate system of the robot arm to obtain the target position and/or pose information of the power mechanism at the coordinate system of the adjacent force applied link and at when the force applied links adjacent to the power mechanism reach the target position and/or pose corresponding to the target position and/or pose information of the respective coordinate systems;

determining if the target position and/or pose information of the power mechanism at the coordinate system of adjacent force applied link is effective;

if it is determined effective, according to the target position and/or pose information of the force applied link closest to the proximal end of robot arm, controlling a movement of the force applied link closest to the proximal end of robot arm and each link at the proximal end of the force applied link to allow the force applied link closest to the proximal end of robot arm to reach the corresponding target position and/or pose; according to the target position and/or pose information of the force applied link farer away from the proximal end of the robot arm, controlling a movement of the force applied link farer away from the proximal end of the robot arm and the links between the force applied link and an adjacent force applied link to allow the force applied link farer away the proximal end of the robot arm to reach a corresponding position and/or pose; and according to target position and/or pose information of the power mechanism, controlling a movement of the power mechanism and the links between the power mechanism and adjacent force applied link to allow the power mechanism to maintain a position thereof while adjusting a pose thereof;

if it is determined ineffective, combining the task degrees of freedom of the power mechanism to analyze the external force of the power mechanism to obtain the target position and/or pose information of the power mechanism at the base coordinate system of the robot arm, and according to the target position and/or pose information of the power mechanism, controlling a movement of each of the plurality of links of the robot arm to allow the power mechanism maintain a position thereof while adjusting a pose thereof.

17. A control method for a robot arm of a surgical robot, the robot arm comprises a plurality of links connected by joints, and one of the plurality of links at a remote end of the robot arm being configured as a power mechanism, wherein, the control method comprises:

determining a force applied link from the plurality of links and acquiring an external force applied on the force applied link;

acquiring an input operating command associated with task degrees of freedom of the power mechanism;

combining the task degrees of freedom of the power mechanism to analyze the external force applied on the force applied link to obtain target position and/or pose information of the force applied link at corresponding coordinate system, and according to the target position and/or pose information, controlling a movement of the robot arm;

wherein, the operating command comprises a first operating command or a second operating command;

the first operating command is associated with a case that the task degrees of freedom being completely matched with effective degrees of freedom of the robot arm, and the acquired target position and/or pose information analyzed according to the first operating command allows a free drag control of the power mechanism;

the second operating command is associated with a case that the task degrees of freedom are not completely matched with the effective degrees of freedom of the robot arm, but included in the effective degrees of freedom of the robot arm, and the acquired target position and/or pose analyzed according to the second operating command allows a drag control of the power mechanism only within a predetermined task degree of freedom.

18. The control method of claim 17, wherein in a situation of the number of the force applied link is one, if the force applied link is the power mechanism, in the step of analyzing the external force applied on the force applied link to acquire the target position and/or pose information of the force applied link at the corresponding coordinate system, and according to the target position and/or pose information, controlling a movement of the robot arm, the control device is configured to perform:

combining the task degrees of freedom of the power mechanism to analyze the external force applied on the force applied link to acquire target position and/or pose information of the power mechanism at a base coordinate system of the robot arm; and according to the target position and/or pose information, controlling a movement of each of the plurality of links of the robot arm to allow the power mechanism to reach a corresponding target position and/or pose.

19. The control method of claim 17, wherein in a situation of the number of the force applied links is two or more, if an acquired input is the first operating command, the step of analyzing the external force applied on the force applied link to acquire the target position and/or information of the force applied link at the corresponding coordinate system, and according to the target position and/or pose information, controlling a movement of the robot arm, comprising:

analyzing the external force applied on the force applied link closest to a proximal end of robot arm to acquire the target position and/or pose information of the force applied link at a base coordinate system of the robot arm;

analyzing the external force applied on the force applied link farer away from the proximal end of the robot arm between each two adjacent force applied links to obtain the target position and/or pose information of the force applied link at the coordinate system of an adjacent force applied link; and according to the target position and/or pose information of the force applied link closest to the proximal end of robot arm, controlling a movement of the force applied link closest to the proximal end of robot arm and each link at the proximal end of the force applied link to allow the force applied link closest to the proximal end of robot arm to reach the target position and/or pose, and according to the target position and/or pose information of the force applied link farer away from the proximal end of the robot arm, controlling a movement of the force applied link farer away from the proximal end of the robot arm and each link between the force applied link and an adjacent force applied link to allow the force applied link farer away the proximal end of the robot arm to reach a corresponding position and/or pose.

20. A control device for a robot arm of a surgical robot, comprising:
   a memory configured for storing a computer program;
   a processor configured for loading and executing the computer program;
   wherein, the computer program is loaded by the processor and carried out by following steps:
   determining a force applied link from the plurality of links and acquiring an external force applied on the force applied link;
   acquiring an operating command associated with task degrees of freedom of the power mechanism; and
   combining the task degrees of freedom of the power mechanism to analyze the external force applied on the force applied link to obtain current target position and/or pose information of the force applied link at a corresponding coordinate system, and according to the target position and/or pose information, controlling a movement of the robot arm;
   wherein, the operating command comprises a first operating command or a second operating command;
      the first operating command is associated with a case that the task degrees of freedom being completely matched with effective degrees of freedom of the robot arm, and the acquired target position and/or pose information analyzed according to the first operating command allows a free drag control of the power mechanism;
      the second operating command is associated with a case that the task degrees of freedom are not completely matched with the effective degrees of freedom of the robot arm, but included in the effective degrees of freedom of the robot arm, and the acquired target position and/or pose analyzed according to the second operating command allows a drag control of the power mechanism only within a predetermined task degrees of freedom.

* * * * *